United States Patent [19]

Chiang et al.

[11] Patent Number: 5,516,679

[45] Date of Patent: May 14, 1996

[54] **PENICILLIN V AMIDOHYDROLASE GENE FROM *FUSARIUM OXYSPORUM***

[75] Inventors: Shu-Jen Chiang, Manlius; William V. Burnett, Jr., Fayetteville; Sean M. Tonzi, Skaneateles, all of N.Y.

[73] Assignee: Bristol-Myers Squibb Company, Princeton, N.J.

[21] Appl. No.: 363,475

[22] Filed: Dec. 23, 1994

[51] Int. Cl.$^6$ ............................. C12N 9/84; C12N 15/55; C12N 15/70; C12N 15/80

[52] U.S. Cl. ................. 435/230; 435/252.33; 435/254.7; 435/320.1; 536/23.2

[58] Field of Search ................... 435/230, 320.1, 435/252.33, 254.7; 536/23.2

[56] References Cited

FOREIGN PATENT DOCUMENTS

WO86/00929 of 0000 WIPO .

OTHER PUBLICATIONS

T. J. White et al., Technical Focus, vol. 5, No. 6, pp. 185–189, 1989.
A. Olsson et al., Applied and Environmental Microbiology, vol. 49, No. 5, pp. 1084–1089, 1985.
A. Olsson et al., Gene, vol. 45, pp. 175–181, 1986.
D. A. Lowe et al., Dev. Ind. Microbial., vol. 22, pp. 163–184, 1981.
D. A. Lowe et al., Biotechnology Letters, vol. 8, No. 3, pp. 151–156, 1986.
Y. Morinaga et al., Biotechnology, vol. 2, pp. 636–639, 1984.
J. W. Taylor et al., Nucleic Acids Research, vol. 13, No. 24, pp. 8749–8764, 1985.
T. A. Kunkel, Proc. Natl. Acad. Sci. USA, vol. 82, pp. 488–492, 1985.
J. R. Sayers et al., Nucleic Acids Research, vol. 16, No. 3, pp. 791–802, 1988.
F. Sanger et al., Proc. Natl. Acad. Sci. USA, vol. 74, No. 12, pp. 5463–5467, 1977.
The Journal of Biological Chemistry, vol. 243, No. 13, pp. 3557–3559, 1968.
R. A. Houghten, Proc. Natl. Acad. Sci. USA, vol. 82, pp. 5131–5135, 1985.
C. Yanisch–Perron et al., Gene, vol. 33, pp. 103–119, 1985.
S. Jain et al., Mol. Gen. Genet., vol. 234, pp. 489–493, 1992.
M. W. Hunkapiller et al., Science, vol. 219, pp. 650–659, 1983.
V. Glisin et al., Biochemistry, vol. 13, No. 12, pp. 2633–2637, 1974.
A. J. Berk et al., Cell, vol. 12, pp. 721–732, 1977.
W. A. Powell et al., Journal of Bacteriology, vol. 172, No. 6, pp. 3163–3171, 1990.
P. Model et al., Cell, vol. 61, pp. 739–741, 1990.
C. Staben et al., Fungal Genet. Lett., vol. 36, pp. 79–81 (1989).
Gubler, U., et al, Gene 25, 263–269, (1983).

*Primary Examiner*—Charles L. Patterson, Jr.
*Attorney, Agent, or Firm*—Thomas R. Savitsky

[57] ABSTRACT

Nucleic acids coding for penicillin V amidohydrolase (PVA) from *Fusarium oxysporum*. Also, expression vectors, host cells and a method for production of PVA.

71 Claims, 20 Drawing Sheets

N-Terminus: Gly-Asn-Asp-Asp-Phe-Ala-[Ala/Lys]-Lys-[ ]-
Ala-Ser-Leu-Lys-Lys-Ser-Leu-Lys-Leu-Pro-Gly-
Thr-[Thr/Val]-Val-Tyr-Phe-Thr-Gln-His-Val Peptide A: Gly-Leu-Asn-[Ser/Pro]-Ser-Gln-[Ala/Leu]-
[Asp/Glu]-Gln-Phe-Tyr-[Tyr/Arg]

Peptide B1: Leu-Val-Lys-Thr-Gly-Pro-Ala-[Ser/Lys]-[ ]-
Val-Ser-Ile

Peptide B2: Gly-Asn-Asp-Asp-Phe-Ala-Ala-[Ser/Lys]-[ ]-
Ala

Peptide C: Gly-[ ]-[Asn/Lys]-Thr-Ala-Asp-Thr-Asn-Val-
Leu-Leu-Ala-[Ile/Arg]-Val-Lys-Trp-Val-Glu-
Glu-Gly Peptide D: Ile-His-Trp-Ser-Gly-Leu-Glu-Asp-Gly-Leu-Ile-
Ser-Ala-Glu-Asn-[Asn/Ser]-Asp-Tyr-Tyr-Asn-
[Asn/His]-Val-[Val/Ser]-Ser-[Thr/Arg]

Peptide E: Pro-Tyr-Asn-Asp

FIG. 1

Amino Acid:     Val-Lys-Trp-Val-Glu-Glu-Gly
Rev.Trans.:     GTN-AAR-TGG-GTN-GAR-GAR-GG
Complement:     CC-YTC-YTC-NAC-CCA-YTT-NAC

```
                        A
Probes:         CC-YTC-YTC-CTC-GGA-YTT-NAC
                        G
                        T
```

| | | | | | | | | | | | |
|---|---|---|---|---|---|---|---|---|---|---|---|
| PVA: | N-TERM | G | N | D | D | F | A | A | K | C | A |

2585 TRANSLATE:                                          V   A   K   C   A

2585 DNA:                                       TTTTTTTGTAGCGAAATGCGCC

2585-M:                                          PST I
                                                   ↓
                                         TTTTTTCTGCAGGAAATGCGCC

2585-FL:
TRANSLATE:            G   N   D   D   F   A   A   K   C   A

CODING STRAND:   CCCGGGAACGACGACTTTGCA-GCGAAATGCGCC
TEMPLATE STRAND: GGGCCCTTGCTGCTGAAA-ACGT CGCTTTACGCGG
                       SMA I
                        ↑

FIG. 3

2585-FL (4490 bps)

Penicillin V Amidohydrolase Gene from F. oxysporum (cDNA)

```
GGCAACGATGATTTTGCCGCGAAATGCGCCAGCCTCAAGAAGTCGCTCAAACTCCCCGGC    60
 G  N  D  D  F  A  A  K  C  A  S  L  K  K  S  L  K  L  P  G

ACCACCGTATACTTCACCCAGCATGTCTCGGCTGGTACCAACATCACTTTCCCCGATAAT   120
 T  T  V  Y  F  T  Q  H  V  S  A  G  T  N  I  T  F  P  D  N

CACCCGACCTGCGGTCCTAACTATCAGGTTACGGACGTTGAGGTCTGCCGCGTGGCCATG   180
 H  P  T  C  G  P  N  Y  Q  V  T  D  V  E  V  C  R  V  A  M

TTAGTCAAGACGGGACCCGCCTCAAACGTTAGCATCGAAGCTTGGCTTCCCTTGAACTGG   240
 L  V  K  T  G  P  A  S  N  V  S  I  E  A  W  L  P  L  N  W

ACAGGTCGGTTCTTAGGAACTGGCAATGGTGGATTAGCTGGCTGTATGCCCTACAACGAT   300
 T  G  R  F  L  G  T  G  N  G  G  L  A  G  C  M  P  Y  N  D

ATGGCGTACGGCAACAGTTTCGGCTTCGCCAGCGTTGGCACGAACAACGGACATAACGGA   360
 M  A  Y  G  N  S  F  G  F  A  S  V  G  T  N  N  G  H  N  G

ACCTCAGGCCTACCCATGTACCGCAACCCAGGCCTGGTTGAGGACTTTGCCTATCGTGCG   420
 T  S  G  L  P  M  Y  R  N  P  G  V  V  E  D  F  A  Y  R  A

GTGCACGCTGGTGCTGTTATCGGAAAGAAGATCACCCAGGGCTTTTACGGCAAGAAGTTC   480
 V  H  A  G  A  V  I  G  K  K  I  T  Q  G  F  Y  G  K  K  F

AAGTCCTACTTTCTCGGCTGCTCGACAGGAGGACGTCAAGCAATGAAGTTGGCACAGAGC   540
 K  S  Y  F  L  G  C  S  T  G  G  R  Q  A  M  K  L  A  Q  S

TTCCCCGAGGATTACGATGGCTATGTGGCAGGTGCTCCGGCTATGCGCTGGAACGGTCTT   600
 F  P  E  D  Y  D  G  Y  V  A  G  A  P  A  M  R  W  N  G  L

CAGGCACGCTCTGGAAGTTTCTGGGGCATCACCGGCCCCCCTGGAGCTCCTGGCCATGTG   660
 Q  A  R  S  G  S  F  W  G  I  T  G  P  P  G  A  P  G  H  V

ACTCCAGACGAGTGGGAAATGGTGCACAAGAGCGTCCTGACTCAGTGCGACGAGCCCATT   720
 T  P  D  E  W  E  M  V  H  K  S  V  L  T  Q  C  D  E  P  I

GATGGCGTCGATGACGGCGTGCTTGAGGACCCCACCCTCTGTCAGTACCGCCCTGAGGCT   780
 D  G  V  D  D  G  V  L  E  D  P  T  L  C  Q  Y  R  P  E  A

CTCATCTGCGGTAAGGGCCAGACCGAGAATTGCCTGACCAAGGCCAAGATTGAGACGGTC   840
 L  I  C  G  K  G  Q  T  E  N  C  L  T  K  A  K  I  E  T  V

CGCAAAGTCTTTTCTCCCCTATACACCACGAATGAGACATACGTCTACCCTCGAGCGGTT   900
 R  K  V  F  S  P  L  Y  T  T  N  E  T  Y  V  Y  P  R  A  V

CCTGGTGCTAACGCTCTCTTTAACTTTGTTGTCGCCGAGACACCATTCGTTTACTCCACA   960
 P  G  A  N  A  L  F  N  F  V  V  A  E  T  P  F  V  Y  S  T

GAATGGTACCAGTATGTCATCTGGGAAGACCCTGAGTGGAATCCTGACACTATTGGGCCC  1020
 E  W  Y  Q  Y  V  I  W  E  D  P  E  W  N  P  D  T  I  G  P
```

FIG. 6A

```
AAGGACTATGATAGAGGTGCCGAGATGAACCCCTATGACATTGAGACTTGGGAGGGAGAC 1080
 K  D  Y  D  R  G  A  E  M  N  P  Y  D  I  E  T  W  E  G  D

CTGTCTAAGTTCCGCAAGCGTGGCAACAAGATGATTCACTGGCACGGCCTTCAGGACGGA 1140
 L  S  K  F  R  K  R  G  N  K  M  I  H  W  H  G  L  Q  D  G

CTCATCAGCGCCGAGAACTCAGACGATTATTATAATCACGTGTCTCGAACAATGGGCCTC 1200
 L  I  S  A  E  N  S  D  D  Y  Y  N  H  V  S  R  T  M  G  L

AATAGTAGCCAGCTGGACCAGTTTTATAGGTTCTTCCGCGTCAGTGGGTGTGGCCATTGC 1260
 N  S  S  Q  L  D  Q  F  Y  R  F  F  R  V  S  G  C  G  H  C

AGCGCCGGAGACGGGGCTTCTCGCATTGGAAACAACGCCGGAAACATGGGCGGCAAGACG 1320
 S  A  G  D  G  A  S  R  I  G  N  N  A  G  N  M  G  G  K  T

GCAGATACTAATGTGCTTCTGGCTATTGTGAAATGGGTCGAGGAAGGCGTTGCGCCAGAA 1380
 A  D  T  N  V  L  L  A  I  V  K  W  V  E  E  G  V  A  P  E
                             [complement to 20mer probe]

ACGATTGGGGGCTACAAGAACGTCGGCGGAACTGCAGATGGCGCTTTTGACTATGAGCGT 1440
 T  I  G  G  Y  K  N  V  G  G  T  A  D  G  A  F  D  Y  E  R

AGGCATTGCCGATACCCACACCGCAATGTCTGGGACGGGAAGGGGAATGTGAAGGATCCC 1500
 R  H  C  R  Y  P  H  R  N  V  W  D  G  K  G  N  V  K  D  P

GATAGCTGGAACTGTAAGATCTGAGGTGTGGCCCTAGGCTTTTGTGGCTGTCGTTAGGTG 1560
 D  S  W  N  C  K  I  *

GCATACGTATATAAGAGGATCACTGTGAACATGCTTTATGTTGTGCAAGAATTGATTGAG 1620

AATCAGATTGAGCTTGCAGAGCCAAGGCAAATAGACCCAACTGTTGACGAGATCTTGGCC 1680

GAAGGTAGAGGCAACGGGGAGAGAGACCATGGAAGACAAGGCGTAGAAAATGGCCGGGGA 1740

AGACGGAAAAAAAAAACCCCCCCCCC                                   1767
```

FIG. 6B

Penicillin V Amidohydrolase Gene from *F. oxysporum* (genomic)

```
AGGTGTCATACGCGTGTACCGAGGTATCACCTCCTTTCTTGGACTATTGGTTGGTTGTTC    60

TATGAAGGACCATCCGTTCACCCCGCAGGAACCAGGGACATCTATGGCAAGAGTTTATCC   120

CGAGGCATGTATATAATAAAGCTCTTGCCTCTCCTTCTCCTGACACTTCTCAGCCAGGCT   180
                                              *Transcription start

CAGGAGGCTGGCAGTGAGTTGAATATCTATCTGTCTGATAGTTGTTCGTCATCAGGCACT   240

ATGCGCGTCAACTTCTCGACCCTGCTGCTTCCAGCCTCCTCCAAGGGCTAGGTGCATGC    300
M   R   V   N   F   S   T   L   L   L   P   S   L   L   Q   G   L   G   A   C

GCAGCTCCCAACAAAGGCAACGATGATTTTGCCGCGAAATGCGCCAGCCTCAAGAAGTCG   360
A   A   P   N   K   G   N   D   D   F   A   A   K   C   A   S   L   K   K   S

CTCAAACTCCCCGGCACCACCGTATACTTCACCCAGCATGTCTCGGCTGGTACCAACATC   420
L   K   L   P   G   T   T   V   Y   F   T   Q   H   V   S   A   G   T   N   I

ACTTTCCCCGATAATCACCCGACCTGCGGTCCTAACTATCAGGTTACGGACGTTGAGGTC   480
T   F   P   D   N   H   P   T   C   G   P   N   Y   Q   V   T   D   V   E   V

TGCCGCGTGGCCATGTTAGTCAAGACGGGACCCGCCTCAAACGTTAGCATCGAAGCTTGG   540
C   R   V   A   M   L   V   K   T   G   P   A   S   N   V   S   I   E   A   W

CTTCCCTTGAACTGGACAGGTCGGTTCTTAGGAACTGGCAATGGTGGATTAGCTGGCTGT   600
L   P   L   N   W   T   G   R   F   L   G   T   G   N   G   G   L   A   G   C

ATGCCCTACAACGATATGGCGTACGGCAACAGTTTCGGCTTCGCCAGCGTTGGCACGAAC   660
M   P   Y   N   D   M   A   Y   G   N   S   F   G   F   A   S   V   G   T   N

AACGGACATAACGGAACCTCAGGCCTACCCATGTACCGCAACCCAGGCGTGGTTGAGGAC   720
N   G   H   N   G   T   S   G   L   P   M   Y   R   N   P   G   V   V   E   D

TTTGCCTATCGTGCGGTGCACGCTGGTGCTGTTATCGGAAAGAAGATCACCCAGGGCTTT   780
F   A   Y   R   A   V   H   A   G   A   V   I   G   K   K   I   T   Q   G   F

TACGGCAAGAAGTTCAAGTCCTACTTTCTCGGCTGCTCGACAGGAGGACGTCAAGCAATG   840
Y   G   K   K   F   K   S   Y   F   L   G   C   S   T   G   G   R   Q   A   M

AAGTTGGCACAGAGCTTCCCCGAGGATTACGATGGCTATGTGGCAGGTGCTCCGGCTATG   900
K   L   A   Q   S   F   P   E   D   Y   D   G   Y   V   A   G   A   P   A   M

CGCTGGAACGGTCTTCAGGCACGCTCTGGAAGTTTCTGGGGCATCACCGGCCCCCCTGGA   960
R   W   N   G   L   Q   A   R   S   G   S   F   W   I   T   G   P   P   G

GCTCCTGGCCATGTGACTCCAGACGAGTGGGAAATGGTGCACAAGAGCGTCCTGACTCAG  1020
A   P   G   H   V   T   P   D   E   W   E   M   V   H   K   S   V   L   T   Q

TGCGACGAGCCCATTGATGGCGTCGATGACGGCGTGCTTGAGGACCCCACCCTCTGTCAG  1080
C   D   E   P   I   D   G   V   D   D   G   V   L   E   D   P   T   L   C   Q
```

FIG. 7A

```
TACCGCCCTGAGGCTCTCATCTGCGGTAAGGGCCAGACCGAGAATTGCCTGACCAAGGCC 1140
 Y  R  P  E  A  L  I  C  G  K  G  Q  T  E  N  C  L  T  K  A

AAGATTGAGACGGTCCGCAAAGTCTTTTCTCCCCTATACACCACGAATGAGACATACGTC 1200
 K  I  E  T  V  R  K  V  F  S  P  L  Y  T  T  N  E  T  Y  V

TACCCTCGAGCGGTTCCTGGTGCTAACGCTCTCTTTAACTTTGTTGTCGCCGAGACACCA 1260
 Y  P  R  A  V  P  G  A  N  A  L  F  N  F  V  V  A  E  T  P

TTCGTTTACTCCACAGAATGGTACCAGTATGTCATCTGGGAAGACCCTGAGTGGAATCCT 1320
 F  V  Y  S  T  E  W  Y  Q  Y  V  I  W  E  D  P  E  W  N  P

GACACTATTGGGCCCAAGGACTATGATAGAGGTGCCGAGATGAACCCCTATGACATTGAG 1380
 D  T  I  G  P  K  D  Y  D  R  G  A  E  M  N  P  Y  D  I  E

ACTTGGGAGGGAGACCTGTCTAAGTTCCGCAAGCGTGGCAACAAGATGATTCACTGGCAC 1440
 T  W  E  G  D  L  S  K  F  R  K  R  G  N  K  M  I  H  W  H

GGCCTTCAGGACGGACTCATCAGCGCCGAGAACTCAGACGATTATTATAATCACGTGTCT 1500
 G  L  Q  D  G  L  I  S  A  E  N  S  D  D  Y  Y  N  H  V  S

CGAACAATGGGCCTCAATAGTAGCCAGCTGGACCAGTTTTATAGGTTCTTCCGCGTCAGT 1560
 R  T  M  G  L  N  S  S  Q  L  D  Q  F  Y  R  F  F  R  V  S

GGGTGTGGCCATTGCAGCGCCGGAGACGGGGCTTCTCGCATTGGAAACAACGCCGGAAAC 1620
 G  C  G  H  C  S  A  G  D  G  A  S  R  I  G  N  N  A  G  N

ATGGGCGGCAAGACGGCAGATACTAATGTGCTTCTGGCTATT GTGAAATGGGTCGAGGAA 1680
 M  G  G  K  T  A  D  T  N  V  L  L  A  I  V  K  W  V  E  E
                                            [complement to 20mer probe]
GGCGTTGCGCCAGAAACGATTGGGGGCTACAAGAACGTCGGCGGAACTGCAGATGGCGCT 1740
 G  V  A  P  E  T  I  G  G  Y  K  N  V  G  G  T  A  D  G  A TTTGACTATGAGCGTAGGCATTGCCGATACCCACACCGCAATGTCTGGGACGGGAAGGGG 1800
 F  D  Y  E  R  R  H  C  R  Y  P  H  R  N  V  W  D  G  K  G AATGTGAAGGATCCCGATAGCTGGAACTGTAAGATCTGAGGTGTGGCCCTAGGCTTTTGT 1860
 N  V  K  D  P  D  S  W  N  C  K  I  *

GGCTGTCGTTAGGTGGCATACGTATATAAGAGGATCACTGTGAACATGCTTTATGTTGTG 1920

CAAGAATTGATTGAGAATCAGATTGAGCTTGCAGAGCCAAGGCAAATAGACCCAACTGTT 1980

GACGAGATCTTGGCCGAAGGTAGAGGCAACGGGGAGAGAGACCATGGAAGACAAGGCGTA 2040

GAAAATGGCCGGGGAAGACGGGCTGTCGGCGATGGAGTAGCAACAGCTGTCACTGGTGGT 2100

CAATGACTACACTTCTGAGCGGCGAGAGATTATAGGGACCGCACACAGGCCATCATTTCC 2160

CGATAACTAATGGAGACGCAATGGAGCGATGTTTAAATGCGACAAGACTGCCATCATCTA 2220

GGTACTTCATGCGTCGCTAAACGCACCAATGCTGCGCTGCTCATGATTGTAAACTTAGTT 2280

TATA                                                       2284
```

PENICILLIN V AMIDOHYDROLASE GENE FROM *FUSARIUM OXYSPORUM*

BACKGROUND OF THE INVENTION

The enzyme penicillin V amidohydrolase is used for enzymatic hydrolysis of penicillin V (phenoxy-methylpenicillin) to 6-aminopenicillanic acid (6-APA). 6-APA is the active beta-lactam nucleus used in the manufacture of semi-synthetic penicillins. Various penicillin V amidohydrolase (PVA) enzymes have been found in fungal, streptomyces and bacterial sources (Lowe et al., 1986, Biotechnol. Lett. 8:151–156). PVA enzyme activity is described by Lowe et al. from a strain of *Fusarium oxysporum*; however, the enzyme was not isolated or purified.

SUMMARY OF THE INVENTION

The present invention concerns an isolated nucleic acid molecule coding for all or part of the PVA from *Fusarium oxysporum* strain 435. The PVA gene has been cloned, sequenced and expressed.

In another aspect, the present invention is directed to a novel promoter from *F. oxysporum* strain 435, expression vectors containing all or part of the PVA gene and/or the novel promoter; and host cells containing the expression vectors. In yet another aspect the present invention is directed to the production of PVA, particularly in the presence of phenoxyacetate as an inducer.

BRIEF DESCRIPTION OF THE DRAWINGS

FIG. 1—The amino acid sequences of six peptide fragments of the intact PVA enzyme. The amino acid sequence of the N-terminus is SEQ. ID. NO.:1, the amino acid sequence of peptide A is SEQ. ID. NO.:2; the amino acid sequence of peptide B1 is SEQ. ID. NO.:3; the amino acid sequence of peptide B2 is SEQ. ID. NO. 4; the amino acid sequence of peptide C is SEQ. ID. NO.:5; the amino acid sequence of peptide D is SEQ. ID. NO.:6; the amino acid sequence of peptide E is SEQ. ID. NO.:7.

FIG. 2—Oligonucleotide probe. A set of four oligonucleotide probes was derived from the reverse transcription of seven amino acids from peptide C (SEQ. ID. NO.:5). The seven amino acid sequence is SEQ. ID. NO.:8; the DNA sequence reversely transcribed from SEQ. ID. NO.:8 is SEQ. ID. NO.:9; the DNA sequence complementary to SEQ. ID. NO.:9 is SEQ. ID. NO.:10; the oligonucleotide probe is SEQ. ID. NO.:11.

FIG. 3—Various DNA and peptide fragments. The PVA N-terminal amino acid sequence is SEQ. ID. NO.:12; the 2585 translate amino acid sequence is SEQ. ID. NO.:13; the 2585 DNA sequence is SEQ. ID. NO.:14; the 2585-M DNA sequence is SEQ. ID. NO.:15; the 2585-FL translate amino acid sequence is identical to SEQ. ID. NO.:12; the 2585-FL DNA sequence of the coding strand is SEQ. ID. NO.:16; the 2585-FL DNA sequence of the template strand (i.e., complementary to the coding strand) is SEQ. ID. NO.:17. All nucleotide sequences (except SEQ. ID. NO.:17) are shown left to right in the 5' to 3' direction.

FIG. 6—PVA cDNA (SEQ. ID. NO.:18) and corresponding amino acid sequence (SEQ. ID. NO.:19). The underlined DNA sequence (base pairs 1348 to 1368 SEQ. ID NO.:20)

2 is complementary to a 20 mer probe (SEQ. ID. NO.:11 ). The asterick indicates a termination codon.

FIG. 7—PVA genomic DNA (SEQ. ID. NO.:21) and corresponding amino acid sequence (SEQ. ID. NO.:22). The promoter is base pair nos. 1 to 240 (SEQ. ID. NO.:23). The first asterisk indicates transcription start and the second asterisk indicates a termination codon.

Figure 8:
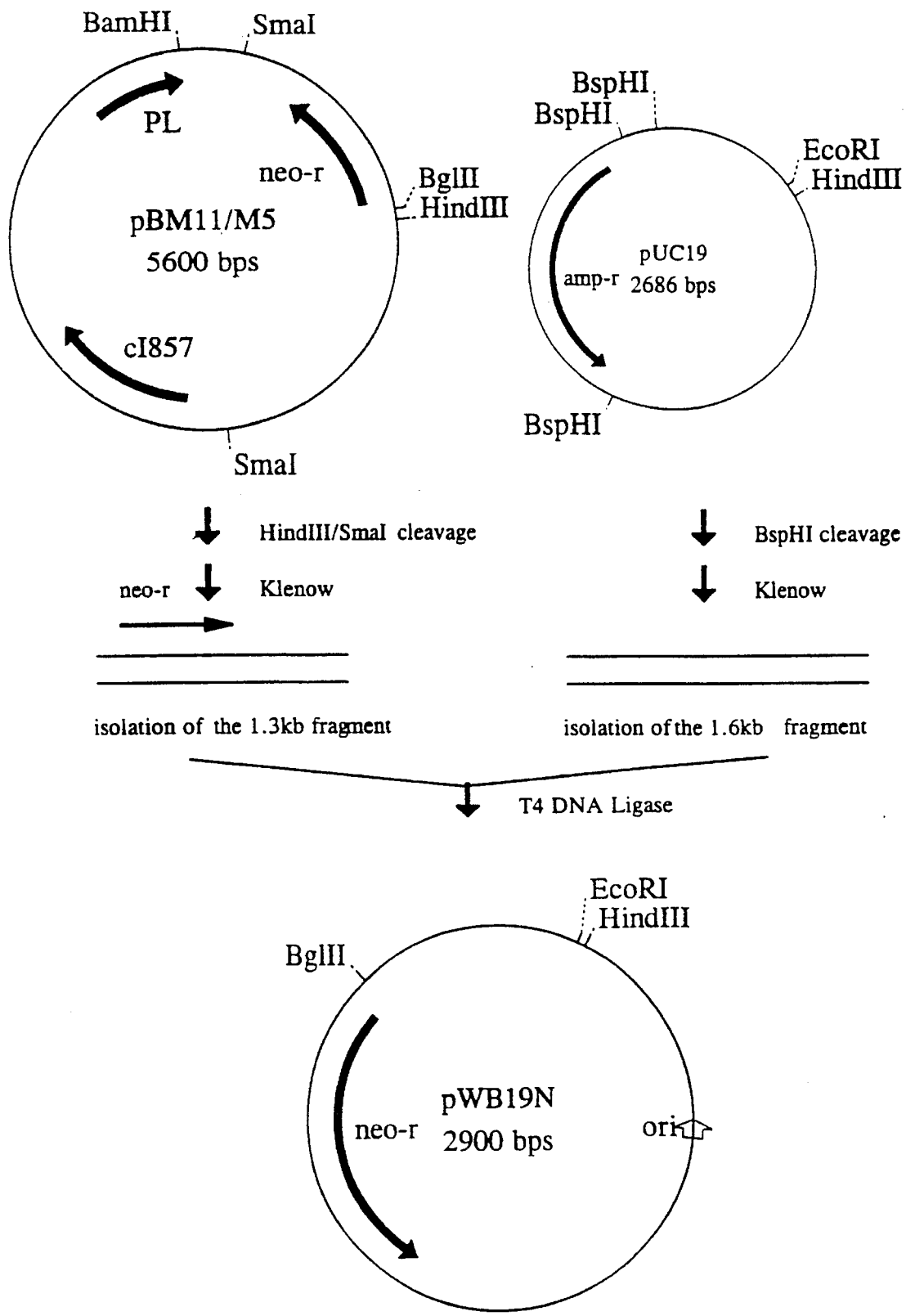

FIG. 8—Schematic representation of construction of pWB19N.

Figure 9:
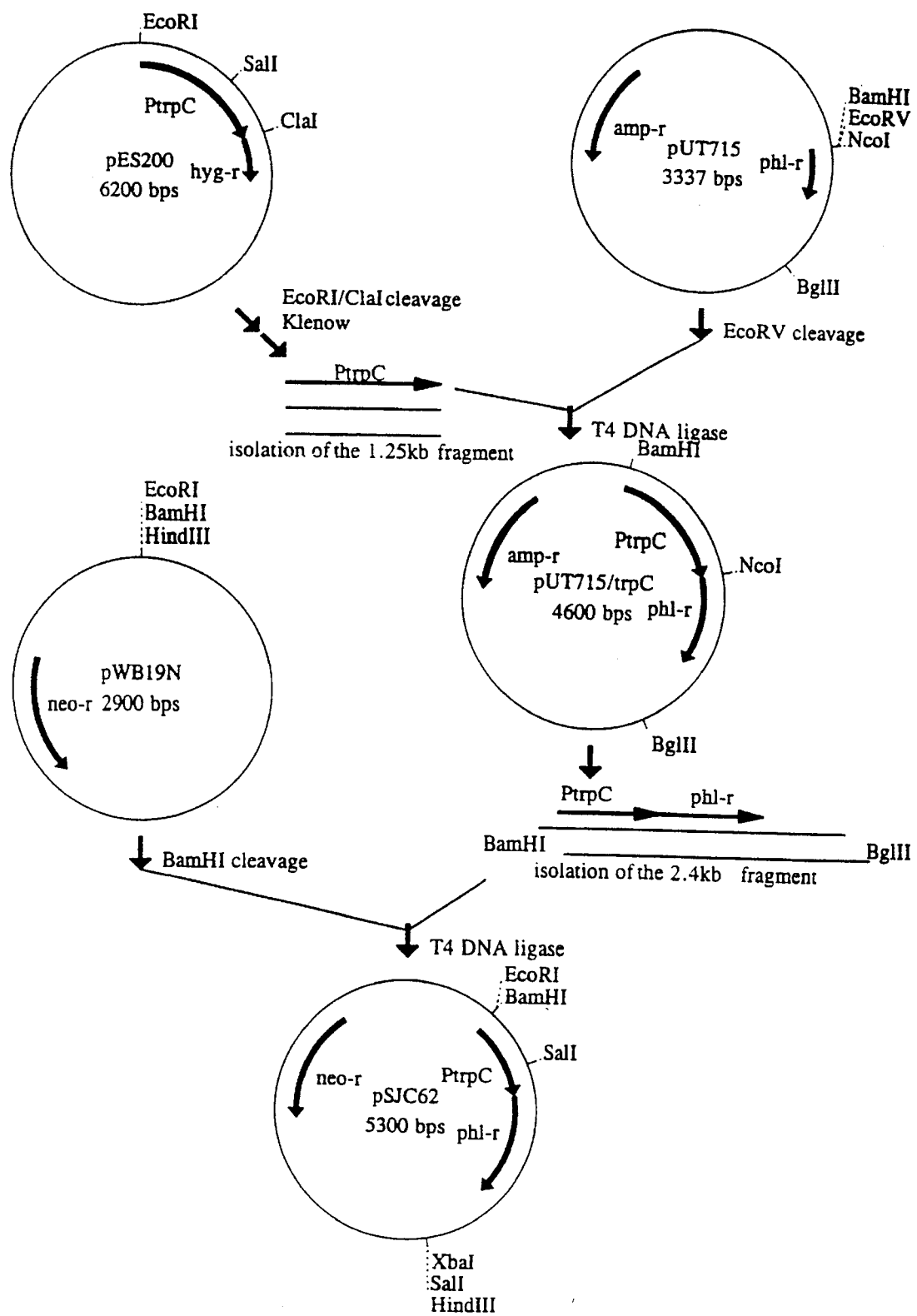

FIG. 9—Schematic representation of construction of pSJC62.

Figure 10:
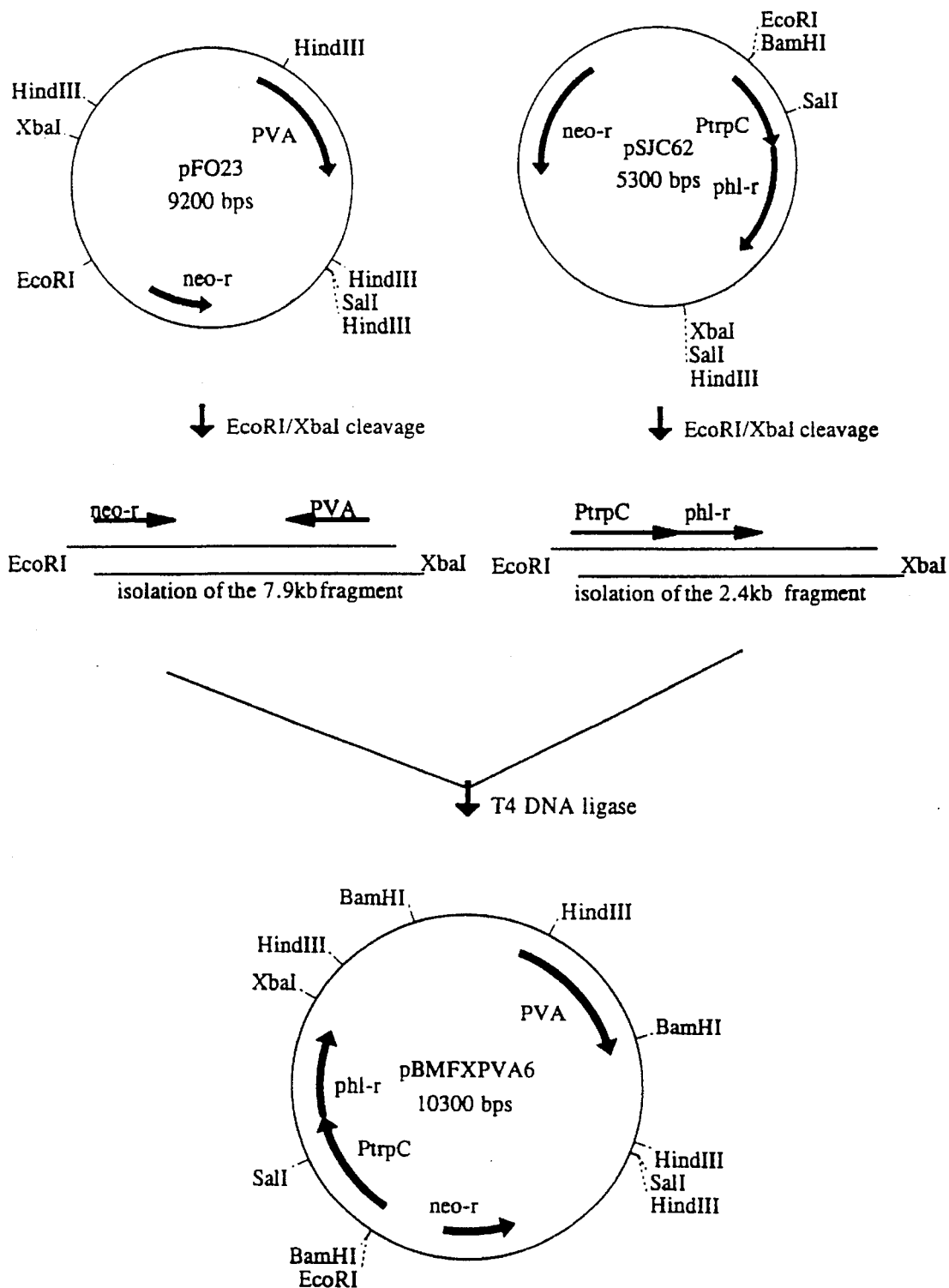

FIG. 10—Schematic representation of construction of pBMFXPVA6.

Figure 11:
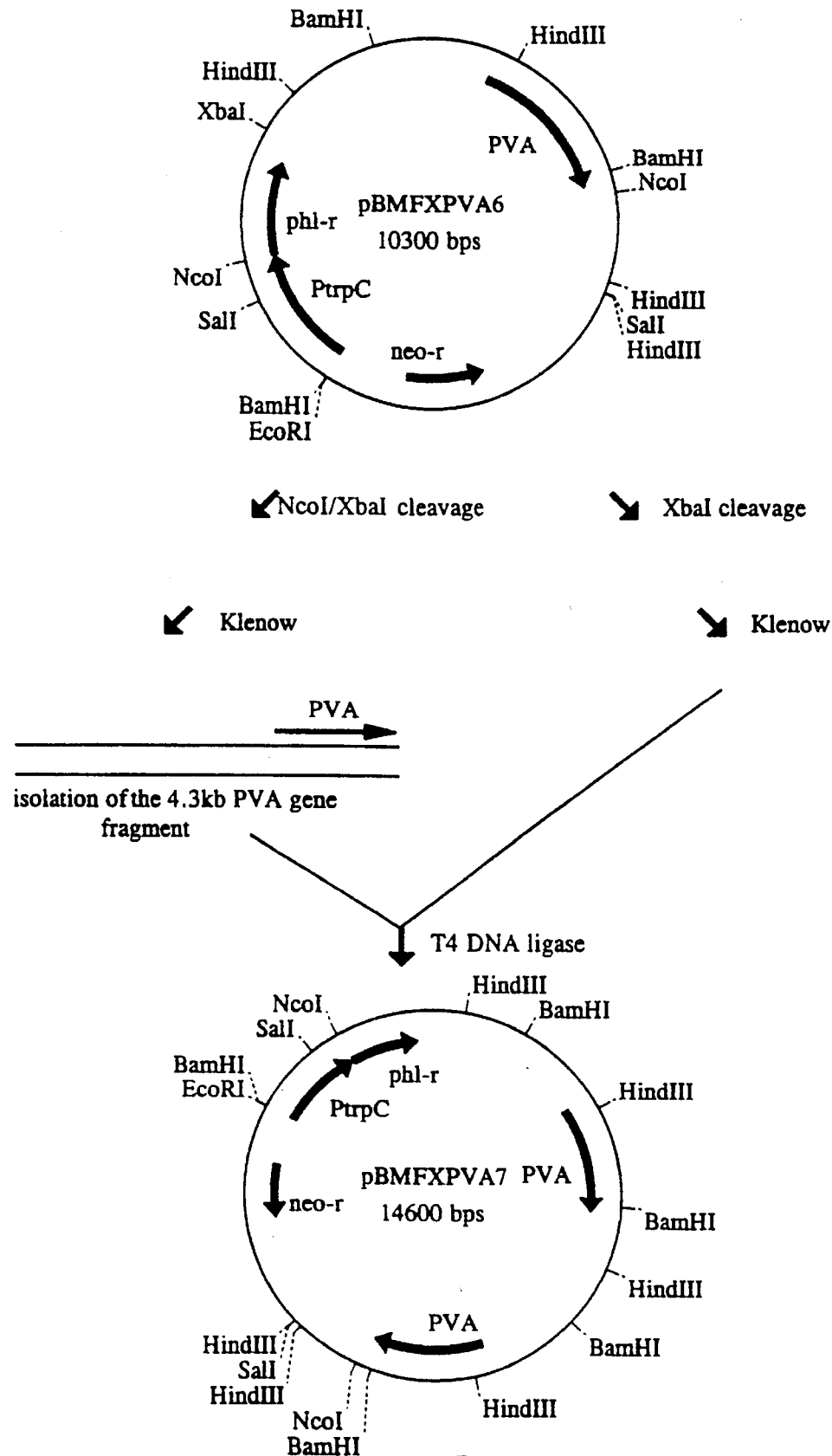

FIG. 11—Schematic representation of construction of pBMFXPVA7.

Figure 12:
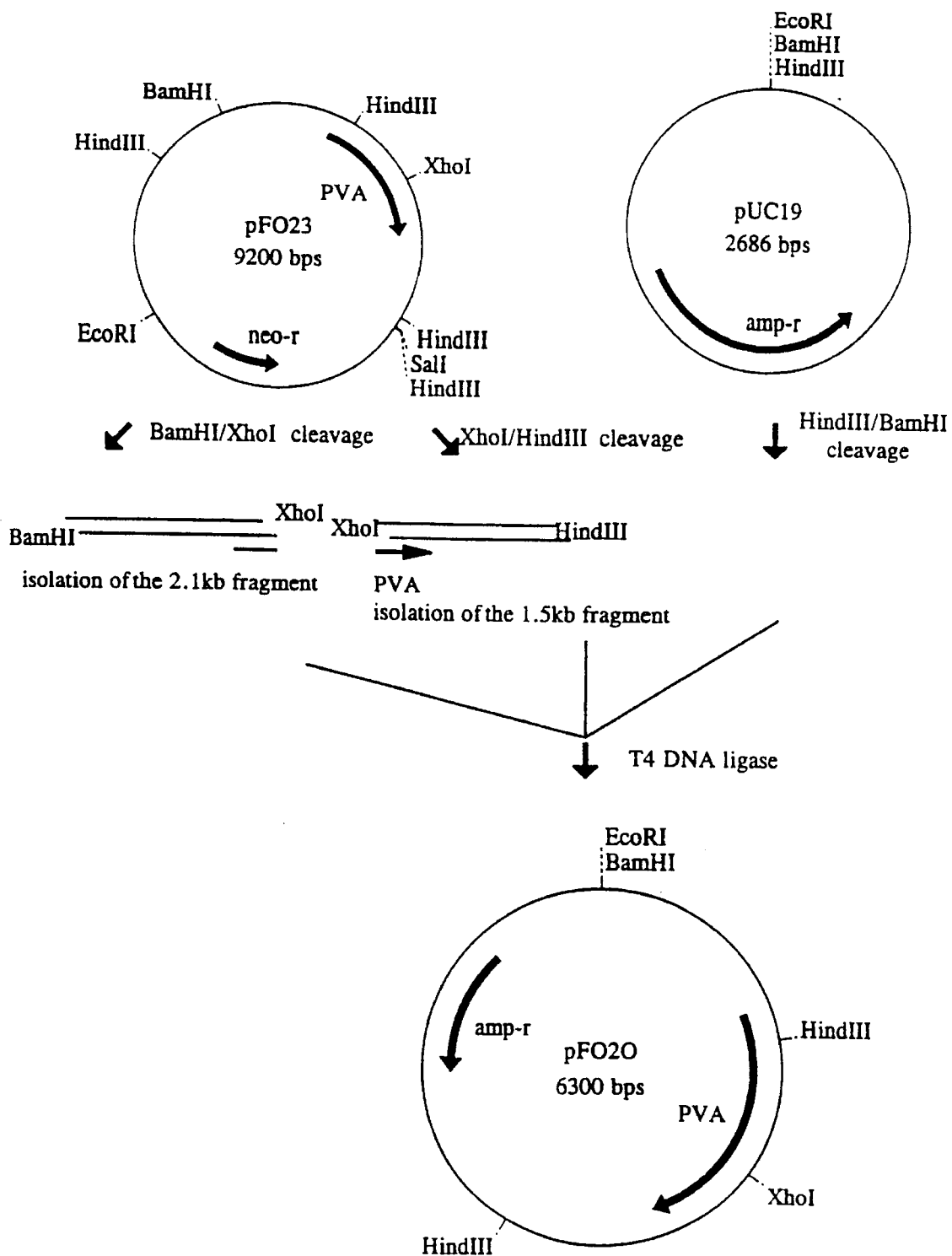

FIG. 12—Schematic representation of construction of pF020.

Figure 13:
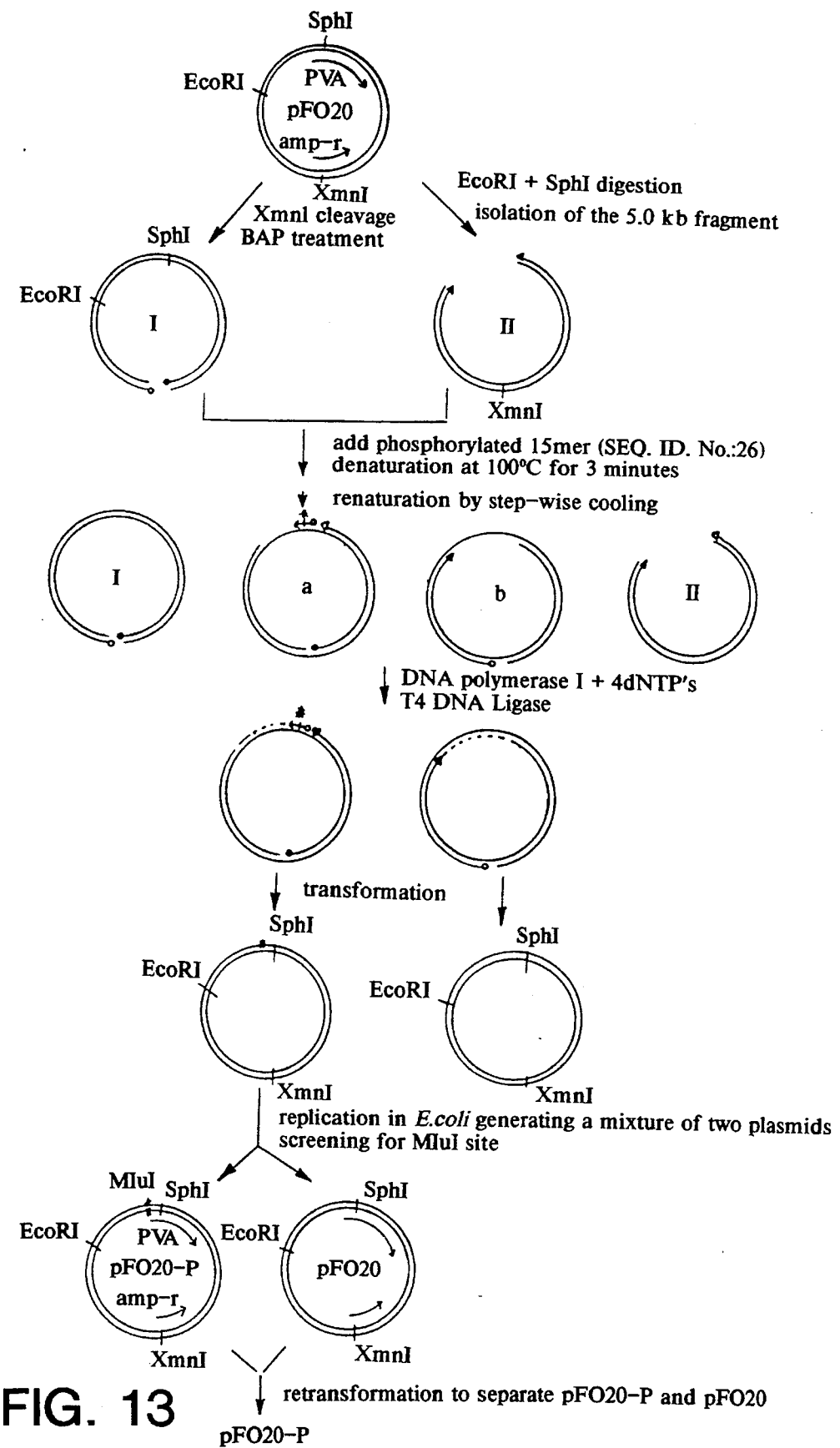

FIG. 13—Schematic representation of construction of pF020-P.

Figure 14:
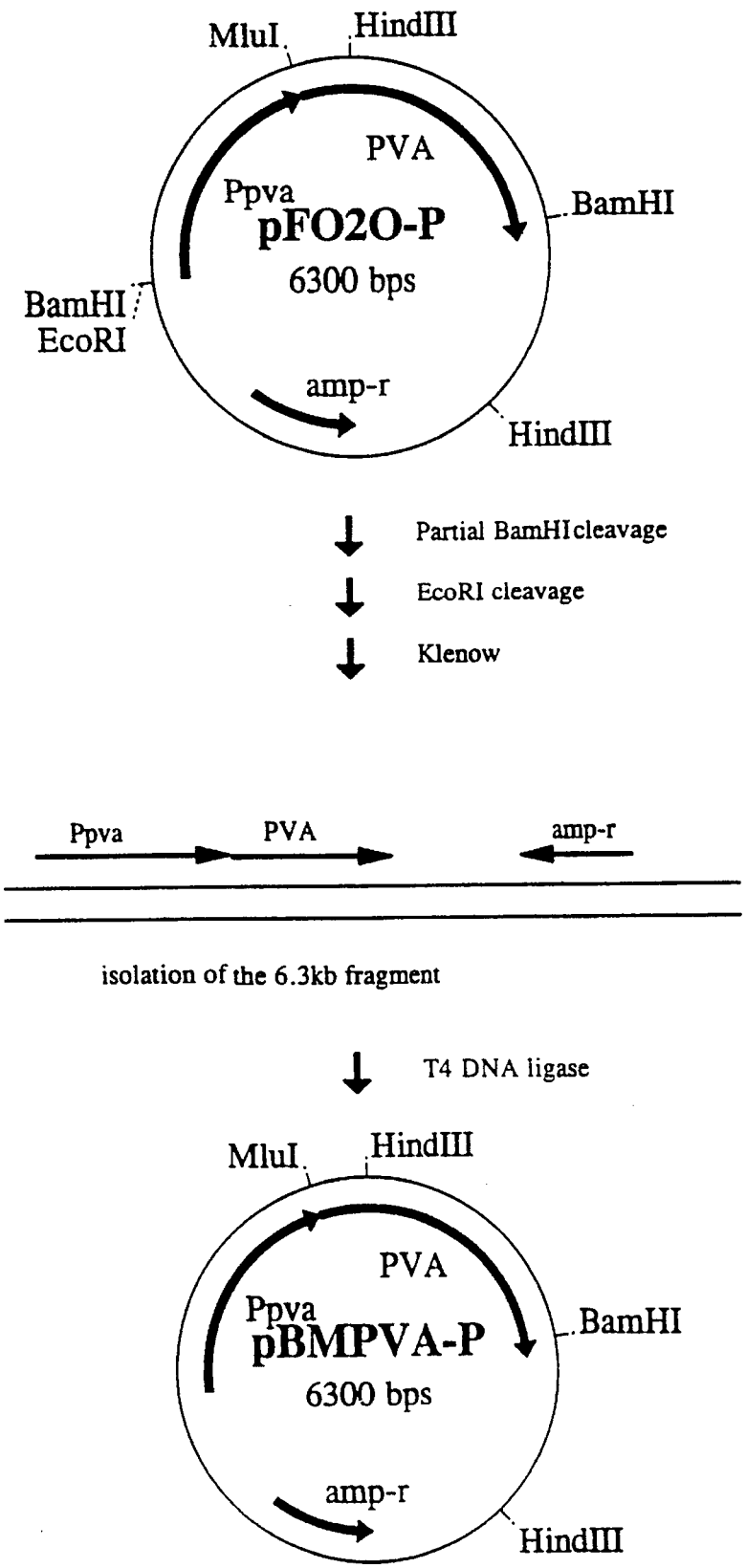

FIG. 14—Schematic representation of construction of pBMPVA-P.

Figure 15:
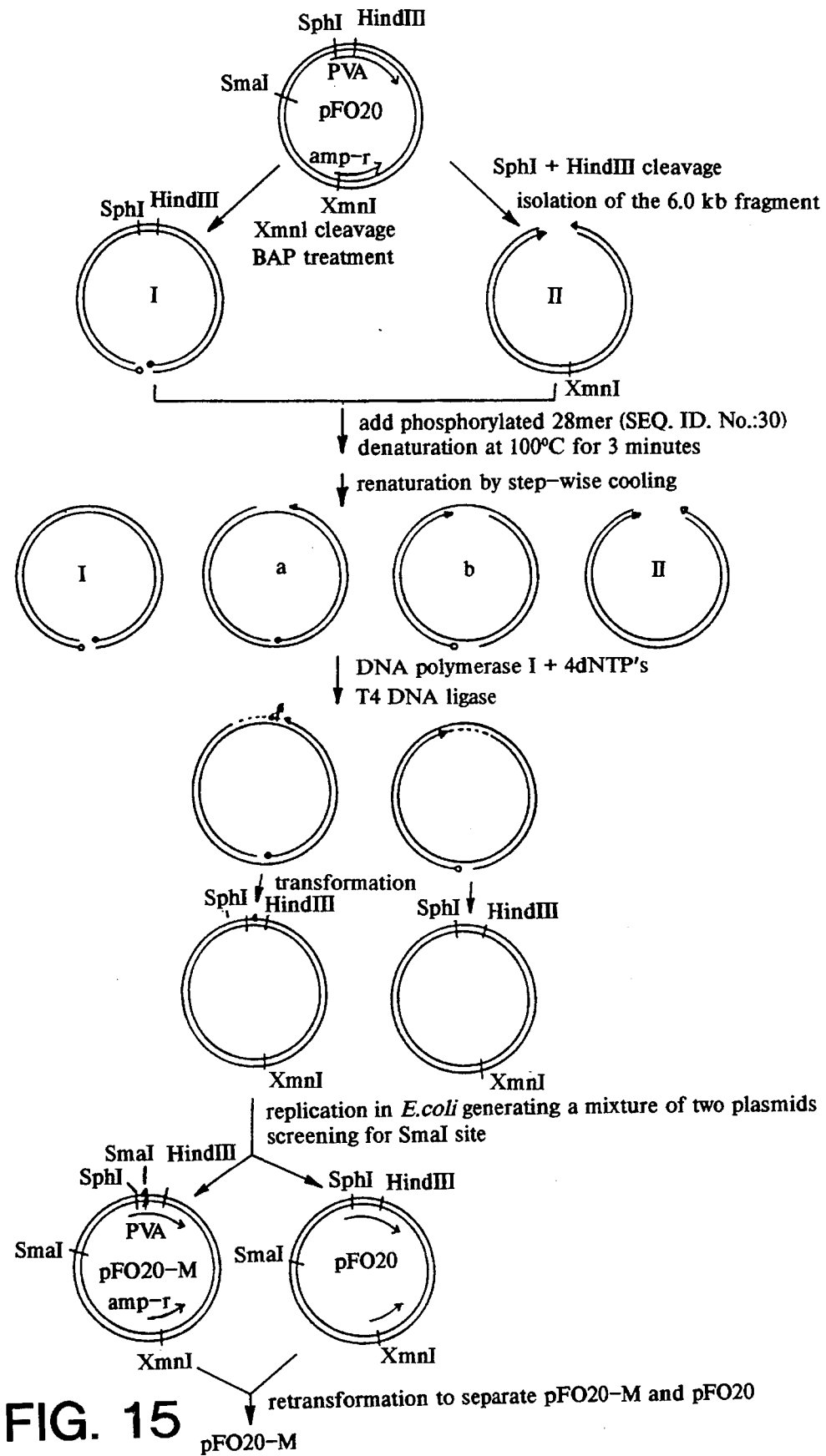

FIG. 15—Schematic representation of construction of pF020-M.

Figure 16:
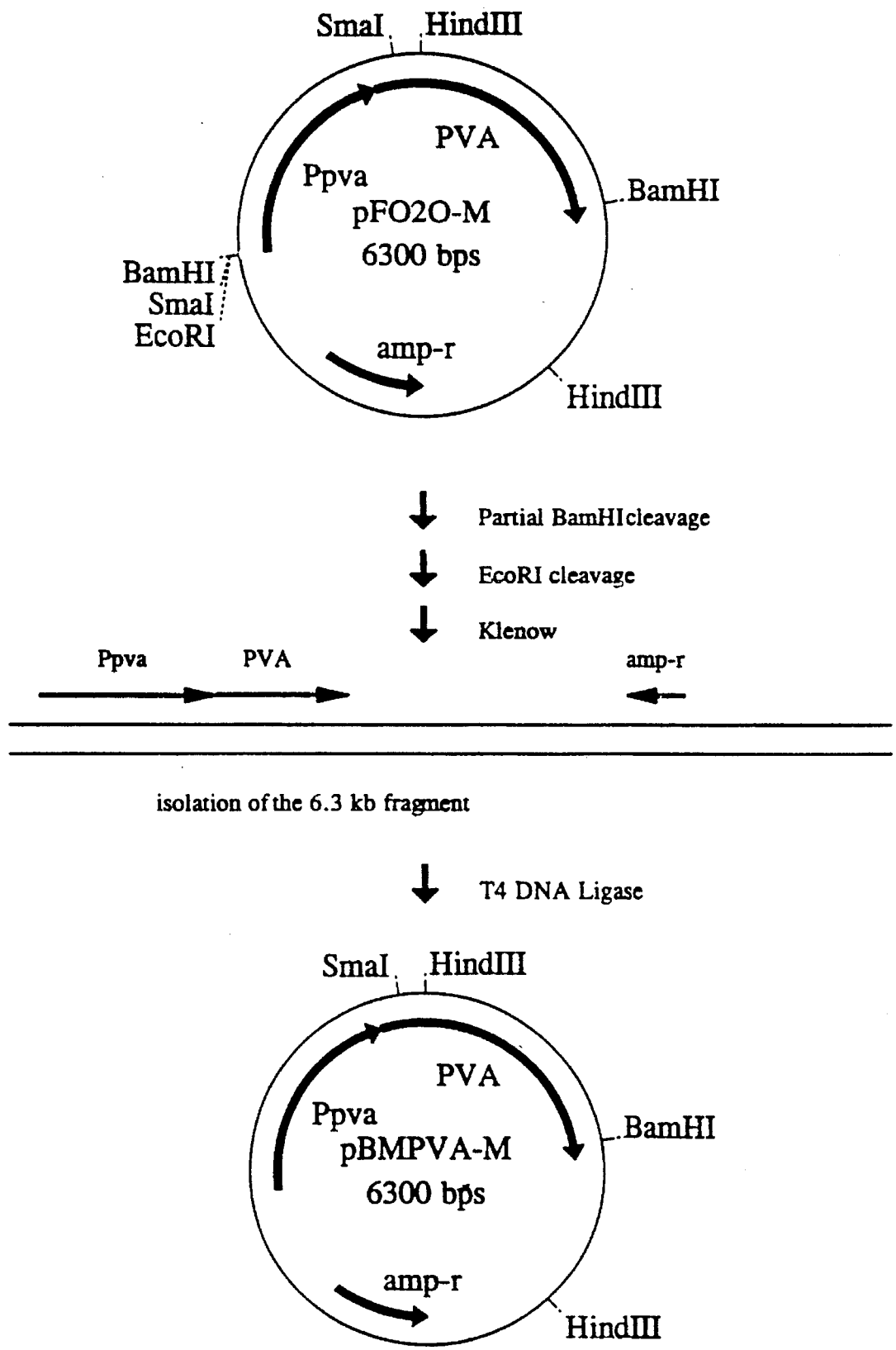

FIG. 16—Schematic representation of construction of pBMPVA-M.

Figure 17:
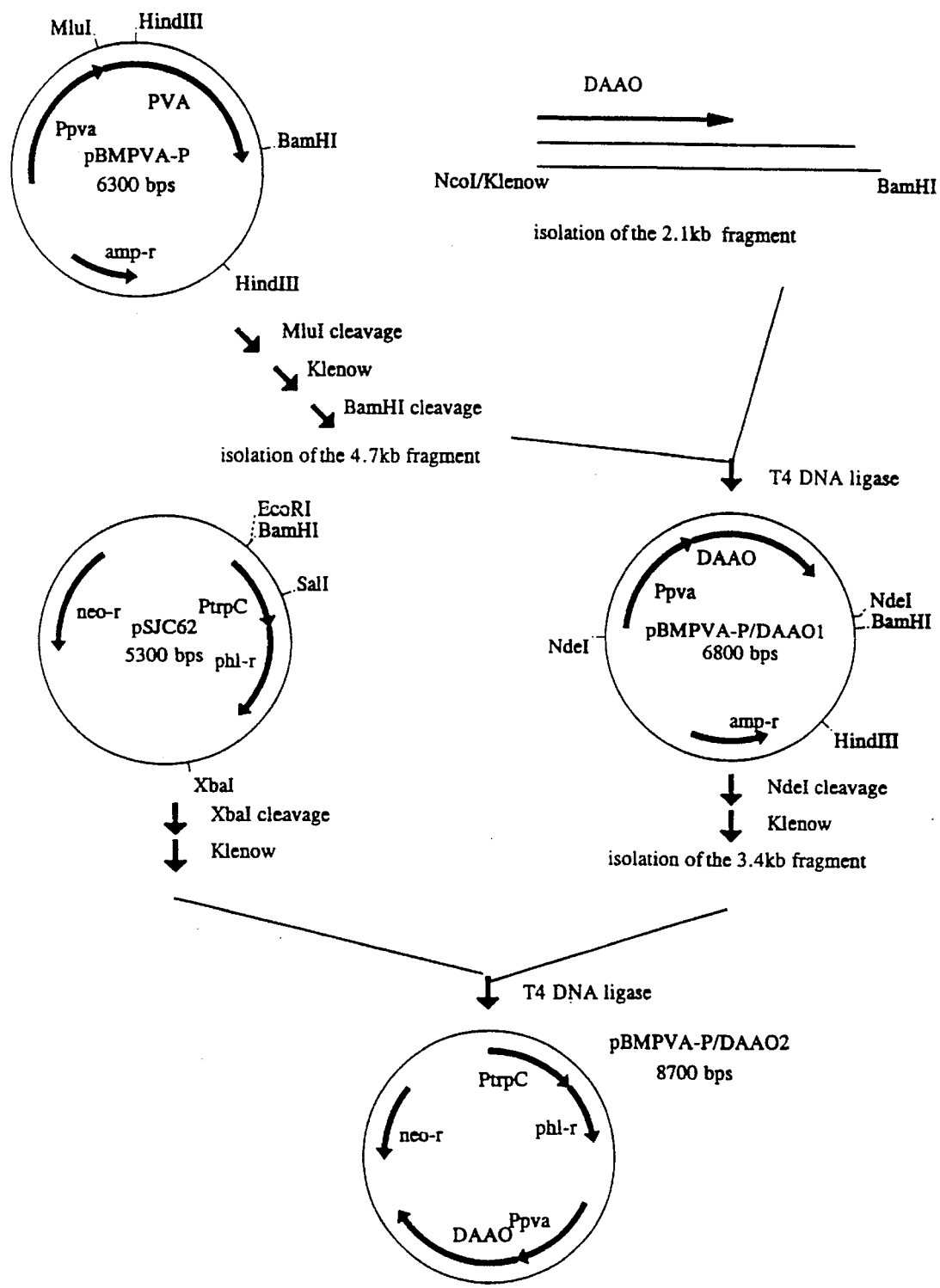

FIG. 17—Schematic representation of construction of pBMPVA-P/DAA02.

Figure 18:
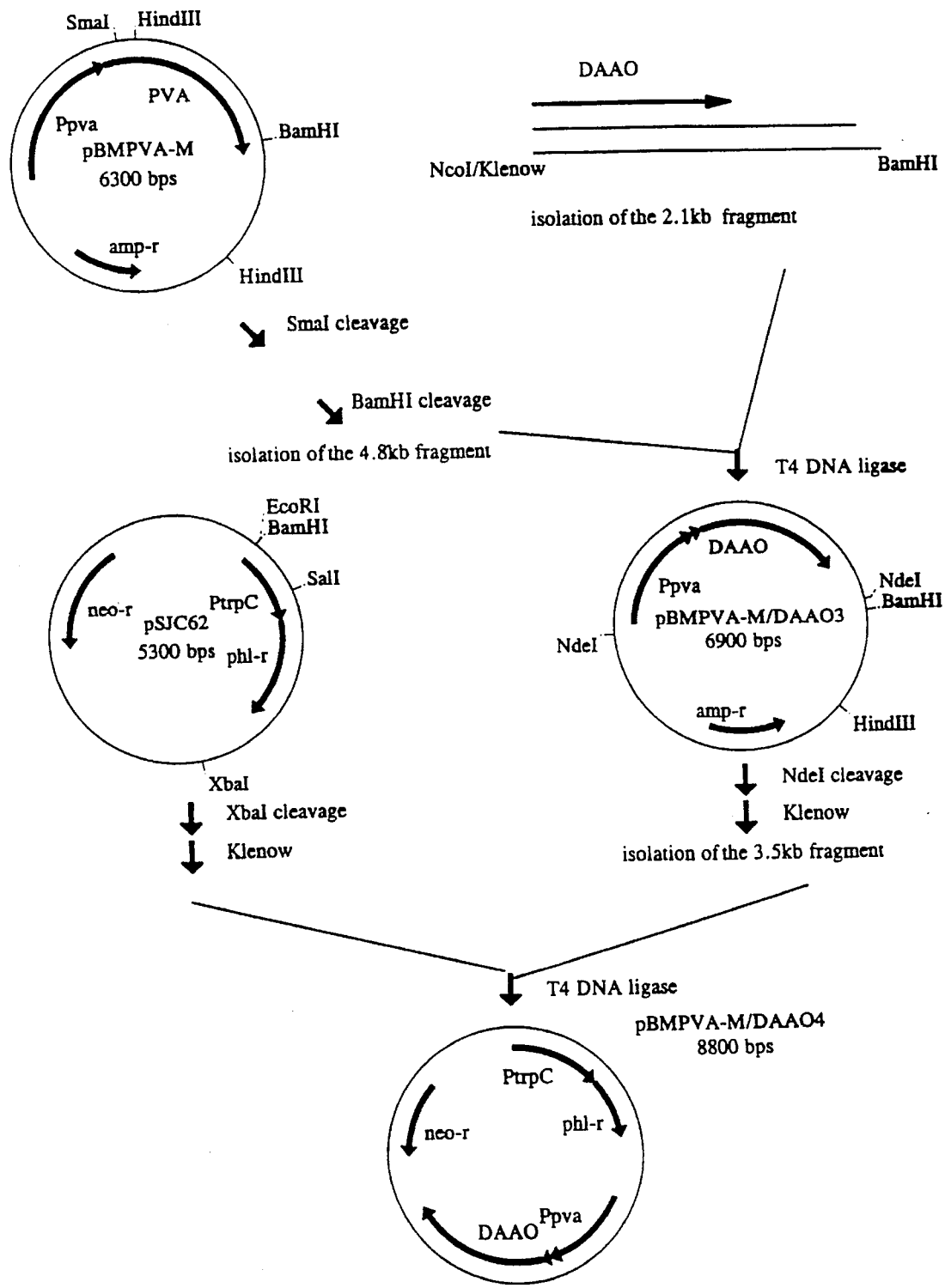

FIG. 18—Schematic representation of construction of pBMPVA-M/DAA04.

DETAILED DESCRIPTION OF THE INVENTION

The present invention concerns an isolated nucleic acid molecule comprising a nucleic acid sequence coding for all or part of PVA from *Fusarium oxysporum*. Preferably, the nucleic acid molecule is a DNA molecule and the nucleic acid sequence is a DNA sequence. All DNA sequences are represented herein by formulas whose left to right orientation is in the conventional direction of 5' to 3' (with the sole exception of SEQ. ID. NO.:17 as shown in FIG. 3). Further preferred is a DNA sequence having all or part of the nucleotide sequence substantially as shown in FIGS. 6 and 7 (particularly SEQ. ID. NO.:18 and SEQ. ID. NO.:21 ); or a DNA sequence complementary to one of these DNA sequences; or a DNA sequence which hybridizes to a DNA sequence complementary to one of these DNA sequences. Preferably, the DNA sequence hybridizes under stringent conditions. "Stringent conditions" means conditions no less stringent than described in the "Detailed Examples of Preferred Embodiments" section hereof. In the case of a nucleotide sequence (e.g., a DNA sequence) coding for part of PVA, it is preferred that the nucleotide sequence be at least about 20 nucleotides in length.

Preferred DNA fragments are the probe of SEQ. ID. NO.:11 and the promoter of SEQ. ID. NO.:23.

The PVA molecules of the present invention do not necessarily need to be catalytically active. For example, catalytically inactive PVA or fragments thereof may be useful in raising antibodies to the protein.

It is also contemplated that the present invention encompasses modified sequences. As used in the present application, the term "modified", when referring to a nucleotide or polypeptide sequence, means a nucleotide or polypeptide sequence which differs from the wild-type sequence found in nature.

The DNA sequences of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library can be screened in order to identify a DNA sequence coding for all or part of PVA. For example, a *F. oxysporum* genomic DNA library can be screened in order to identify the DNA sequence coding for all or part of PVA. Various techniques can be used to screen the genomic DNA or cDNA libraries.

For example, labeled single stranded DNA probe sequences duplicating a sequence present in the target genomic DNA or cDNA coding for all or part of PVA can be employed in DNN/DNA hybridization procedures carried out on cloned copies of the genomic DNA or cDNA which have been denatured to single stranded form.

A genomic DNA or cDNA library can also be screened for a genomic DNA or cDNA coding for all or part of PVA using immunoblotting techniques.

In one typical screening method suitable for either immunoblotting or hybridization techniques, the genomic DNA library, which is usually contained in a vector, or cDNA library is first spread out on agar plates, and then the clones are transferred to filter membranes, for example, nitrocellulose membranes. A DNA probe can then be hybridized or an antibody can then be bound to the clones to identify those clones containing the genomic DNA or cDNA coding for all or part of PVA.

In the second approach, the DNA sequences of the present invention coding for all or part of PVA can be chemically synthesized. For example, the DNA sequence coding for PVA can be synthesized as a series of 100 base oligonucleotides that can be sequentially ligated (via appropriate terminal restriction sites or complementary terminal sequences) so as to form the correct linear sequence of nucleotides.

In the third approach, the DNA sequences of the present invention coding for all or part of PVA can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White et al., Trends Genet. 5, 185–189 (1989).

The DNA sequences of the present invention can be used in a variety of ways in accordance with the present invention. The most apparent use of the DNA sequence is to prepare PVA to be useful for conversion of penicillin V to 6-APA. However, they also can be used as DNA probes to screen other cDNA and genomic DNA libraries as to select by hybridization other DNA sequences that code for proteins related to PVA. In addition, the DNA sequences of the present invention coding for all or part of PVA can be used as DNA probes to screen other cDNA and genomic DNA libraries to select by hybridization DNA sequences that code for PVA molecules from organisms other than *Fusarium oxysporum*.

The DNA sequences of the present invention coding for all or part of PVA can also be modified (i.e., mutated) to prepare various mutations. Such mutations may be either degenerate, i.e., the mutation changes the amino acid sequence encoded by the mutated codon, or non-degenerate, i.e., the mutation does not change the amino acid sequence encoded by the mutated codon. These modified DNA sequences may be prepared, for example, by mutating the PVA DNA sequence so that the mutation results in the deletion, substitution, insertion, inversion or addition of one or more amino acids in the encoded polypeptide using various methods known in the art. For example, the methods of site-directed mutagenesis described in Morinaga et al., Bio/Technol. 2, 636–639 (1984), Taylor et al., Nucl. Acids Res. 13, 8749–8764 (1985) and Kunkel, Proc. Natl. Acad. Sci. U.S.A. 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers et al., Nucl. Acids Res. 16, 791–802 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the present invention.

The present invention is also particularly directed to the novel promoter for PVA which is shown in FIG. 7 (SEQ. ID. NO.:23). The novel promoter of the invention can be used with other known DNA sequence coding for other useful proteins or polypeptides.

The present invention further concerns expression vectors comprising a DNA sequence coding for all or part of PVA and/or the promoter for PVA. The expression vectors preferably contain all or part of one of the DNA sequences having the nucleotide sequences substantially as shown in FIGS. 6 or 7. Further preferred are expression vectors comprising one or more regulatory DNA sequences operatively linked to the DNA sequence coding for all or part of PVA. As used in this context, the term "operatively linked" means that the regulatory DNA sequences are capable of directing the replication and/or the expression of the DNA sequence coding for all or part of PVA.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front (i.e., upstream of) the DNA sequence (preferably the promoter of SEQ. ID. NO.:23) and followed by the DNA sequence coding for all or part of a structural protein such as PVA, D-amino acid oxidase, monoclonal antibodies, insulin, interferon, epidermal growth factor, growth hormone, and the like. The DNA sequence coding for all or part of the structural protein is followed by transcription termination sequences and the remaining vector. The expression vectors may also include other DNA sequences known the art, for example, stability leader sequences which provide for stability of the expression product, secretory leader sequences which provide for secretion of the expression product, sequences which allow expression of the structural gene to modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a fungal cell system, the expression vector should contains promoters isolated from the genome of fungal cells (e.g., the trpC promoter from *Aspergillus nidulans* and the PVA promoter from *Fusarium oxysporum*). Certain expression vectors may contain a fungal autonomously replicating sequence (ARS; e.g., ARS from *Fusarium oxysporum* and *Saccharomyces cerevisiae*) which promotes in vivo production of self-replicating plasmids in fungal hosts. It is preferred that the fungel expression vectors of the invention do not have a fungel ARS sequence and thus will integrate into host chromosomes upon plasmid entry of host cells. Such integration is preferred because of enhanced genetic stability. An expression vector as contemplated by the present invention is at least capable of directing the replication in *Escherichia coli* and integration in fungel cells, and preferably the expression, of the PVA DNA sequences of the present invention. Suitable origins of replication in *E. coli* vadous hosts include, for example, a ColEl plasmid replication origin. Suitable promoters include, for example, the trpC promoter from *Aspergillus nidulans*, the PVA promoter from *F. oxysporum*, and the neo-r gene promoter from *E. coli*. Suitable termination sequences include, for example, the trpC terminator from *A. nidulans*, the PVA terminator for *F. oxysporum*, and the neo-r gene terminator from *E. coli*. It is also preferred that the expression vector include a sequence coding for a selectable marker. The selectable marker is preferably antibiotic resistance. As selectable markers, phleomycin resistance (for fungal cells), ampicillin resistance, and neomycin resistance (for bacterial cells) can be conveniently employed. All of these materials are known in the art and are commercially available.

Particularly preferred is the expression vector designated pBMFXPVA6, described herein below and in FIG. 10, which contains the DNA sequence coding for PVA, or expression vectors with the identifying characteristics of pBMFXPVA6. Also preferred are the expression vectors designated pWB19N, pSJC62, pBMFXPVA7, pBMPVA-P and pBMPVA-M, described herein below and in FIGS. 8, 9, 11, 14 and 16, respectively, or expression vectors with the identifying characteristic of pWB19N,, pSJC62, pBMFX-PVA7, pBMPVA-P, and pBMPVA-M.

Host cell *Escherichia coil* DH5α strain containing pBM-FXPVA7, pBMPVA-P and pBMPVA-M were deposited with the American Type Culture Collection, Rockville, Md. on Dec. 14, 1994 under the Budapest Treaty and assigned ATCC accession nos. 69721, 69722 and 69720, respectively.

Suitable expression vectors containing the desired coding and control sequences may be constructed using standard recombinant DNA techniques known in the art, many of which are described in Sambrook et al. Molecular Cloning: A Laboratory Manual, 2nd edition, Cold Spring Harbor Laboratory, Cold Spring Harbor, N.Y. (1989).

The present invention additionally concerns host cells containing an expression vector which comprises a DNA sequence coding for all or part of PVA, and/or the promoter of SEQ. ID. NO.:23. The host cells preferably contain an expression vector which comprises all or part of one of the DNA sequence having the nucleotide sequences substantially as shown in FIGS. 6 or 7. Further preferred are host cells containing an expression vector comprising one or more regulatory DNA sequences capable of directing the replication and/or the expression of and operatively linked to a DNA sequence coding for all or part of PVA. Additionally included are host cells containing an expression vector which comprises a DNA sequence which has been modified (e.g., disrupted, deleted or truncated) so as to code for a PVA molecule which is not catalytically active. Suitable host cells include both eukaryotic and prokaryotic host cells, for example, *Escherichia coli* cells. Suitable eukaryotic host cells include, for example, *Cephalosporium acremonium*, *Fusarium oxysporum* and *Penicillium chrysogenum* cells.

Particularly preferred as host cells are *Fusarium oxysporum* strains.

Expression vectors may be introduced into host cells by various methods known in the art. For example, transfection of host cells with expression vectors can be carried out by the polyethylene glycol mediated protoplast transformation method. However, other methods for introducing expression vectors into host cells, for example, electroporation, biolistic injection, or protoplast fusion, can also be employed.

Once an expression vector has been introduced into an appropriate host cell, the host cell may be cultured under conditions permitting expression of large amounts of the desired polypeptide, in the preferred case a polypeptide molecule comprising all or part of PVA.

Host cells containing an expression vector which contains a DNA sequence coding for all or part of PVA may be identified by one or more of the following six general approaches: (a) DNA-DNA hybridization; (b) the presence or absence of marker gene functions; (d) assessing the level of transcription as measured by the production of PVA mRNA transcripts in the host cell; (d) detection of the gene product immunologically; (e) colorimetric detection; and (f) enzyme assay, enzyme assay being the preferred method of identification.

In the first approach, the presence of a DNA sequence coding for all or part of PVA can be detected by DNA-DNA or RNA-DNA hybridization using probes complementary to the DNA sequence.

In the second approach, the recombinant expression vector host system can be identified and selected based upon the presence or absence of certain marker gene functions (e.g., acetamide utilization, resistance to antibiotics, resistance to fungicide, uracil prototrophy, etc.). A marker gene can be placed in the same plasmid as the DNA sequence coding for all or part of PVA under the regulation of the same or a different promoter used to regulate the PVA coding sequence. Expression of the marker gene in response to induction or selection indicates the presence of the entire recombinant expression vector which carries the DNA sequence coding for all or part of PVA.

In the third approach, the production of PVA mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of PVA can be assessed immunologically, for example, by Western blotting.

In the fifth approach, the expression of PVA protein can be assessed by complementation analysis. For example, in cells known to be deficient in this enzyme, expression of PVA activity can be detected on the enzymatic hydrolysis of a colorless substrate, phenoxyacetic-p-nitroanilide, to a yellow colored p-nitroaniline on the media plate.

In the sixth approach, expression of PVA can be measured by assaying for PVA enzyme activity using known methods. For example, the assay described in the "Detailed Examples of the Preferred Embodiments" section hereof may be employed.

The DNA sequences of expression vectors, plasmids or DNA molecules of the present invention may be determined by various methods known in the art. For example, the dideoxy chain termination method as described in Sanger et al., Proc. Natl. Acad. Sci. U.S.A. 74, 5463–5467 (1977), or the Maxam-Gilbert method as described in Proc. Natl. Acad. Sci. U.S.A. 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for producing PVA comprising culturing a host cell containing an expression vector capable of expressing PVA. Preferably the expression vector is pBMFXPVA6 or pBMFXPVA7. It has been surprisingly found that the production of PVA is substantially enhanced in the presence of phenoxyacetate which acts as an inducer.

The present invention further concerns polypeptide molecules comprising all or part of PVA, said polypeptide molecules preferably having all or part of one of the amino acid sequences substantially as shown in FIGS. 6 or 7. In the case of polypeptide molecules comprising part of PVA, it is preferred that polypeptide molecules be at least about 10 amino acids in length.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |

-continued

| TABLE OF CORRESPONDENCE | | |
|---|---|---|
| SYMBOL | | |
| 1-Letter | 3-Letter | AMINO ACID |
| D | Asp | L-aspartic acid |
| N | Asn | L-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described in Houghton et al., Proc. Natl. Acad. Sci. 82, 5131–5135 (1985) may be employed. It is preferred that the polypeptides be obtained by production in prokaryotic or eukaryotic host cells expressing a DNA sequence coding for all or part of PVA, or by in vitro translation of the mRNA encoded by a DNA sequence coding for all or part of PVA. For example, the DNA sequence of FIG. 6 or 7 may be synthesized using PCR as described above and inserted into a suitable expression vector, which in turn may be used to transform a suitable host cell. The recombinant host cell may then be cultured to produce PVA. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

In addition to preparing 6-APA, the polypeptides of the present invention may be used in a wide variety of other ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from vadous sources.

The polypeptides of the present invention have been defined by means of determined DNA and deduced amino acid sequencing. Due to the degeneracy nature of the genetic code, which results from there being more than one codon for most of the amino acid residues and stop signals, other DNA sequences which encode the same amino acid sequence as depicted in FIGS. 6 and 7 may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphatic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the aforementioned polypeptides, as well as precursors of the aforementioned polypeptides, for example, precursors having N-terminal substituents such as methionine, N-formylmethionine used and leader sequences. All such variations are included within the scope of the present invention.

The following examples are further illustrative of the present invention. These examples are not intended to limit the scope of the present invention, and provide further understanding of the invention.

DETAILED EXAMPLES OF PREFERRED EMBODIMENTS

In the examples, microbial strains, plasmids, buffer, growth media and common methods are described as follows.

Microbial Strains and Plasmids

The plasmids, bacterial and fungal strains used are listed in Table 1.

TABLE 1

Figure 5:
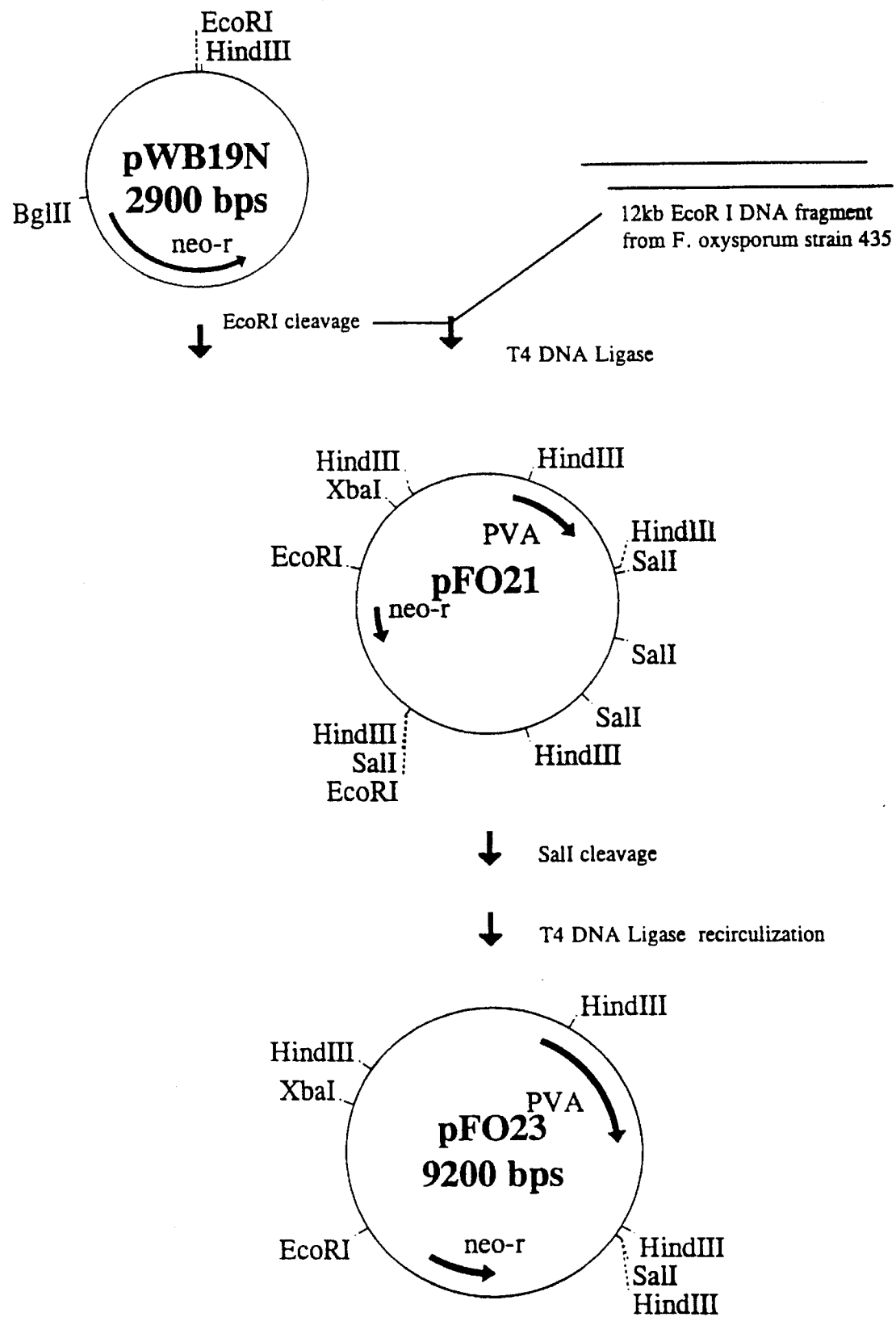
FIG. 5—Schematic representation of cloning of the genomic PVA gene.

| Strains and Plamids | Relevant Charcteristics | Reference |
|---|---|---|
| Escherichia coli DH5α | F-φ80d/acZΔM15 Δ(lacZYA-argF)U169 deoR recA1 endA1 hsdR17 ($r_k^- m_k^-$) supE44 λ-thi-1 gyrA96 relA1 | Life Technologies, Inc. |
| Fusarium oxysporum strain 435 | Penicillin V amidase producer | novel isolate |
| Fusarium oxysporum f.sp. lycopersici | ATCC strain | ATCC 16322 |
| pBM11/M5 | $Neo^R$, 5.6 kb | ATCC 67436 |
| pES200 | $Amp^R$, $Hyg B^R$, 6.2 kb | (1) |
| pUC19 | $Amp^R$, 2686 bp | (2) |
| pUT715 | $Amp^R$, 3337 bp | (3) |
| pUT715/trpC | $Amp^R$, $Phl^R$, 4.6 kb | *, FIG. 9 |
| pWB19N | $Neo^R$, 2.9 kb | *, FIG. 8 |
| pSJC62 | $Neo^R$, $Phl^R$, 5.3 kb | *, FIG. 9 |
| pFO20 | $Amp^R$, $PVA^+$, 6.3 kb | *, FIG. 12 |
| pFO20-P | $Amp^R$, $PVA^+$, 6.3 kb | *, FIG. 13 |
| pFO20-M | $Amp^R$, $PVA^+$, 6.3 kb | *, FIG. 15 |
| pFO21 | $Neo^R$, $PVA^+$, 15 kb | *, FIG. 5 |
| pFO23 | $Neo^R$, $PVA^+$, 9.2 kb | *, FIG. 5 |
| pBMFXPVA6 | $Neo^R$, $Phl^R$, $PVA^+$, 10.3 kb | *, FIG. 10 |
| pBMFXPVA7 | $Neo^R$, $Phl^R$, $PVA^+$, 14.6 kb | *, FIG. 11 |
| pBMPVA-P | $Amp^R$, $PVA^+$, 6.3 kb | *, FIG. 14 |
| pBMPVA-M | $Amp^R$, $PVA^+$, 6.3 kb | *, FIG. 16 |
| pBMPVA-P/DAAO1 | $Amp^R$, $DAAO^+$, 6.8 kb | *, FIG. 17 |
| pBMPVA-DAAO2 | $Neo^R$, $Phl^R$, $DAAo^+$, 8.7 kb | *, FIG. 17 |
| pBMPVA-M/DAAO3 | $Amp^R$, $DAAO^+$, 6.9 kb | *, FIG. 18 |
| pBMPVA-M/DAAO4 | $Neo^R$, $Phl^R$, $DAAO^+$, 8.8 kb | *, FIG. 18 |

(1) Staben et al., 1989, Fungal Genet. Lett. 36:79–81.
(2) Yanisch-Perron et al., 1985, Gene 33:103–119.
(3) Jain et al., Mol. Gen. Genet. 234:489–493.
*Described hereinafter.

Buffers and Media

Luria broth: 1% Difco Bacto tryptone, 0.5% Difco Bacto yeast extract, 0.5% sodium chloride.

Luria agar: Luria broth supplemented with 1.5% Difco Bacto agar.

SOC media: 2% Difco Bacto tryptone, 0.5% Difco Bacto yeast extract, 10 mM NaCl, 2.5 mM KCl. After autoclaving, add one hundredth volume of 1M $MgCl_2$, 1M $MgSO_4$, and 20% glucose to the medium.

Fusarium vegetative growth medium: 6% starch, 4% Pharmamedia (Trader Protein, Memphis, Tenn.), 0.3% $(NH_4)_2SO_4$, 0.75% $KH_2PO_4$, 0.75% $K_2HPO_4$, adjusted to pH 6.8 with 10N NaOH.

PVA production medium: Fusarium vegetative growth medium supplemented with 0.4% phenoxyacetate.

Tris-EDTA buffer (TE): 10 mM Tris-HCl (pH 7.4), 1 mM EDTA.

Tris-acetate electrophoresis buffer (TAE): 40 mM Tris-acetate (pH 8.0), 1 mM EDTA.

20X SSC: 3M NaCl, 0.3M sodium citrate, adjusted to pH 7.0 with 10N NaOH.

20X SSPE: 3M NaCl, 0.2M $NaH_2PO_4$, 20 mM EDTA, adjusted to pH 7.4 with 10N NaOH.

50X Denhardt solution: 1% Ficoll, 1% polyvinylpyrrolidone, 1% bovine serum albumin (BSA).

30X NET: 4.5M NaCl, 0.45M Tris-HCl (pH 7.5), 30 mM EDTA.

Methods

General cloning techniques, DNA sequencing and plasmid DNA extraction from E. coli were used as described in Sambrook et al. 1989, "Molecular Cloning: A Laboratory Manual", 2nd edition, Cold Spring Harbor Laboratory, CSH, N.Y. All restriction enzymes and DNA modifying enzymes were obtained from commercial supplies. They were used according to the manufacture's instructions. Other frequently used methods were carried out as follows.

1. Electro-Transformation of E. coli (Electroporation)

Four ml of a fresh overnight culture of E. coli DH5α cells was inoculated into 400 ml of Luria broth and grown by shaking at 37° C. to an $OD_{600}$ of 0.6. Cells were harvested by chilling on ice for 15 minutes and centrifuging in a cold rotor at 7,000 x g for 10 minutes. The cell pellet was washed twice in 200 ml of 0° C. water and once in 10 ml of 0° C. 10% glycerol. The cell pellet was resuspended to a final volume of 1 ml (1 to $3\times10^{10}$ cells/ml) in 0° C. 10% glycerol. The cell suspension was frozen in 40 µl aliquotes per 1.5 ml polypropylene tube on dry ice and stored at −70° C.

The frozen cells were thawed at room temperature and then immediately placed on ice. About 2–3 µl of DNA in TE or in ligation mixture was added to the cells, gently mixed and set on ice for 1 minute. The mixture was then transferred to a prechilled 0.2 cm electroporation cuvette (Bio-Rad catalog #165-2086, BioRad Laboratories, Inc.). The Bio-Rad Gene Pulser apparatus (BioRad catalog #165-2075) was set at 25 µF for capacitance and 2.50 KV for voltage. The Pulse Controller (Bio-Rad catalog #165-2098) was set to 200 ohms for resistance. The cuvette was pulsed once at these settings. After electroporation, 1 ml of SOC medium was added to the cuvette. The cell suspension was transferred with a Pasteur pipet to a 17×100 mm polypropylene tube and incubated at 37° C. for 1 hour. Cells were plated on a selective medium (Luria agar with neomycin or ampicillin at a concentration of 40 μg/ml or 100 μg/ml, respectively).

2. Fusarium Protoplast Transformation

*Fusarium oxysporum* strains were cultured in 20 ml potato dextrose broth (PDB; Difco Laboratories) at 24° C. Microconidia were filtered through a layer of 30 μm mesh nylon filter (Spectra/Mesh Nylon N, Spectrum Medical Industries, Inc.). The microconidia were pelleted by centrifugation at 1,500 x g for 8 minutes at room temperature. The microconidia were washed twice in sterile distilled water. Approximately $1 \times 10^{10}$ microconidia were germinated in 100 ml of PDB by shaking for 15 hours at 24° C. The germinated microconidia were collected by centrifugation at 1,500 x g for 8 minutes at room temperature in sterile 50 ml conical tubes. The pellet was washed twice with 0 buffer (1.4M $MgSO_4$, 50 mM sodium citrate, pH 5.8). The germinated microconidia were treated with 20 ml of O buffer containing 2% of Novozyme 234 (BioSPacific, Inc.) at 24° C. for 1 to 2 hours. When greater than 90% of the protoplasts were formed, the mixture were centrifuged in two 15 ml conical tubes at 900 x g at 4° C. for 30 minutes. The protoplasts were gently pipeted from the top of the suspension and washed twice in T buffer (1.2M sorbitol, 50 mM $CaCl_2$, 10 mM Tris-HCl, pH 7.4) at 4° C. The protoplasts were suspended at $1 \times 10^9$ per ml in T buffer containing 6% polyethylene glycol-4000 and 1% dimethylsulfoxide. The protoplasts were frozen in small aliquotes per 1.5 ml polypropylene tube on dry ice and stored at $-70°$ C.

The protoplasts were transformed by thawing a frozen suspension at room temperature and adding a nuclease inhibitor, aurintricarboxylate, to a final concentration of 2 mM. Ten to twenty μg of plasmid DNA in 10 μl TE was added to 200 μl of the protoplast suspension and incubated for 30 minutes on ice. A solution of 60% polyethylene glycol-4000/50 mM $CaCl_2$ was added in two 200 μl and one 800 μl volumes with gentle mixing between each addition and was incubated for 30 minutes on ice. Then 10 ml of 1.2M sorbitol/0.5X PDB was added and gently mixed. The protoplasts were pelleted by centrifugation at 900 x g for 8 minutes at 4° C. The pellet was suspended in 0.5 ml of 1.2M sorbitol/0.5X PDB. One tenth ml of the protoplast suspension was spread on a 1.2M sorbitol/0.1X PDB/1.5% agar plate which had been freshly poured in two layers. The bottom layer contained 12.5 ml medium with phleomycin at a concentration of 75 μg per ml, which slowly diffused into the 12.5 ml medium in the top layer. The plates were incubated at 24° C. for 7 days. The transformants were verified by the growth on a 1X PDA medium containing phleomycin at a concentration of 20 μg/ml and by DNA dot-blot hybridization with the plasmid DNA probe.

3. Extraction of Chromosonal DNA from Fusarium Strains

Fusarium protoplasts were prepared as described in the Fusarium protoplast transformation section. After protoplasts were collected from the top of the suspension and washed twice in T buffer at 4° C., the protoplasts were resuspended in 4 ml of lysis buffer [0.7M NaCl, 10 mM Tris-HCl, pH 8.0, 10 mM EDTA and 1% sodium dodecyl sulfate (SDS)], gently mixed and incubated at 37° C. for 5 minutes. One tenth volume of 10% hexadecyltdmethylammonium bromide (CTAB) in 0.7M NaCl was added to the protoplast lysate, gently mixed and incubated at 65° C. for 15 minutes. Chromosomal DNA was extracted by the addition of an equal volume of chloroform:isoamyl alcohol mixture (24:1). The aqueous solution was collected and six tenths volume of isopropanol was added to precipitate the chromosomal DNA. The DNA was collected by centrifugation at 1,500 x g for 5 minutes at room temperature. The DNA was washed once with 70% ethanol, added under vacuum. The DNA was resuspended in 1 ml of TE with 200 μg of ribonuclease A (EC 3.1.27.5, from Sigma Chemical Co.) per ml and incubated at 37° C. for 20 minutes. A preparation of proteinase K solution (EC 3.4.21.14, from Boehringer Mannheim, GmbH) was added to a final concentration of 400 μg/ml and the DNA solution was incubated at 37° C. for 20 minutes. One tenth volume of 3M NaCl was added and DNA solution was extracted two times with an equal volume of phenol:chloroform:isoamyl alcohol (25:24:1) mixture. The aqueous solution was collected and two volumes of ethanol was added to precipitate the chromosomal DNA. The DNA was then collected by centrifugation at 1,500 xg for 5 minutes at room temperature. The DNA was washed once with 70% ethanol, added under vacuum and resuspended in 1 ml TE.

4. DNA Labeling

DNA probes were made from plasmid DNA or agarose purified DNA fragments and labeled with $\alpha$-$^{32}$P-dCTP (Amersham Corp.) using the Nick translation System (Life Technologies, Inc.). Oligonucleotide probes were phosphorylated with $\gamma$-$^{32}$P-ATP (Amersham Corp.) using T4 polynucleotide kinase enzyme. Before each use of the labeled probes, DNA probes were heat denatured at 100° C. for 5 minutes and quickly cooled on ice for 2 minutes.

5. DNA Dot-Blot Hybridization

DNA samples were heat denatured in a total volume of 0.4 ml with 0.4M NaOH, 10 mM EDTA at 100° C. for 10 minutes and loaded on a Bio-Rad Zeta-probe GT membrane (Bio-Rad Laboratories, Inc.) or a nitrocellulose membrane (Minifold, Schleicher & Schnell, Inc.) under vacuum in a dot-blot apparatus (Minifold, Schleicher & Schnell, Inc.). Hybridization was carried out in a hybridization oven (Laboratory Products Sales, Inc.). The Zeta-probe GT membrane was placed in a bottle and prehybridized with 5 ml of hybridization buffer (0.5M $Na_2HPO_4$, pH 7.2, 7% SDS) at 65° C. for 2 hours with rotation. Then the solution was replaced with 5 ml of freshly prepared hybridization buffer. The labeled DNA probe was added and hybridization was carded out for 16 to 24 hours at 65° C. with rotation. The hybridized membrane was washed twice at 65° C. for 30 minutes each in buffer consisting of 40 mM $Na_2HPO_4$ (pH 7.2) and 5% SDS. The membrane was subsequently washed twice at 65° C. in buffer consisting of 40 mM $Na_2HPO_4$ (pH 7.2) and 1% SDS. When nitrocellulose membrane was used, the hybridization was carried out in a similar condition, except that the composition of the hybridization buffer was 6X SSC, 5X Denhardt solution, 10 mM potassium phosphate (pH 7.2), 0.1% SDS and 250 μg of denatured salmon sperm DNA per mi. The hybridized membrane was washed twice at 65° C. for 30 minutes each with 2X SSC-0.1% SDS, followed by two 30 minutes washes at 65° C. with 0.1X SSC- 0.1% SDS. If oligonucleotide probe was used, the temperature of hybridization and wash were maintained at 50° C. After washing, the membrane was exposed to Kodak XAR-5 X-ray film (Eastman Kodak Co.) for autoradiography.

6. Southern DNA Hybridization

Fusarium chromosomal DNA was digested to completion with each of several different restriction enzymes and electrophoresed through a 0.8% agarose gel in TAE buffer with 0.25 μg ethidium bromide per ml. The gel was treated by acid depurination, alkaline denaturation and neutralization as described in Sambrook et al. and transferred to a Bio-Rad Zeta-probe GT membrane or a nitrocellulose membrane using Bio-Rad Model 785 Vacuum Blotter (Bio-Rad catalog #165-5000). DNA hybridization and autoradiography were carried out as described above.

7. Penicillin V Amidohydrolase Enzyme Assay

Conidia from *Fusarium oxyporum* strains were isolated for 1-week-old potato dextrose agar (PDA, Difco Laboratories) plates by washing the surface with 5 ml of sterile distilled water. One half ml of conidia solution was inoculated into 25 ml Fusarium vegetative growth medium in a 125 ml flask. The vegetative culture was grown for 72 hours on a rotary shaker (250 rpm) at 24° C. and two tenth ml aliquote of the negetative culture was inoculated into 25 ml PVA production medium in a 125 ml flask. The culture was carried out on a rotary shaker at 24° C. for 144 hours.

Production cultures were first diluted in a 5 mM potassium phosphate buffer (pH 7.5). One ml of an appropriately diluted culture was added to 1 ml of 3% penicillin V solution made in 25 mM potassium phosphate buffer (pH 7.5). The reaction mixture was shaken at 35° C. for 15 minutes and stopped by adding 1 ml of 6% (w/v) trichloroacetic (TCA) solution. The mixture was centrifuged at 1,500 x g for 8 minutes. One ml of the cleared supernatant was added to 3 ml p-dimethylaminobenzaldehyde (p-DAB) working solution which was made by mixing 1 part of 1% p-DAB in 100% methanol with 6 parts of glacial acetic acid: $H_2O$: 1N NaOH mixture (40:19:1 ratio). The mixture was incubated at room temperature for 5 minutes and taken optical density measurement at a wavelength of 415 nm. A control tube containing 1 ml of 6-APA at 100 μg/ml and 3 ml of p-DAB working solution yielded a 0.27 optical density reading at 415 nm. The enzyme activity (IU/ml) is calculated by using the optical density reading at 415 nm multiplied by the dilution factor and multiplied by 0.34. Penicillin V amidohydrolase activity is expressed as international units (IU), one unit equivalent to the conversion of 1 μmole of penicillin V per minute under the above assay condition.

EXAMPLE 1

Penicillin V Amidase Amino Acid Sequence

The secreted form of the PVA enzyme was isolated, purified and characterized. It is a glycoprotein with a molecular weight of 65 kilodaltons. Purified enzyme was digested with cyanogen bromide. Gel filtration chromatography of cyanogen bromide-digested PVA on sephadex G-100 allowed the purification of six major fragments, A, B1, B2, C, D, and E. The N-terminal amino acid sequence of six peptide fragments as well as the intact PVA molecule was determined by automated Edman degradation method (Hunkapiller and Hood, 1983, Science 219:650–659). The peptide sequence information obtained is as shown in FIG. 1.

EXAMPLE 2

Penicillin V Amidase cDNA Cloning

1. Extraction of mRNA from *Fusarium oxysporum* strain 435

*Fusarium oxysporum* strain 435 cells were grown in PVA production medium, washed with resuspended guanidine isothiocyanate buffer, and sonicated to break open the cells. Total RNA was isolated by centrifugation through a CsCl cushion (Glisin et al, 1974, Biochem. 13:2633–2837). mRNA was prepared by oligo(dT) chromatography (Sambrook et al., 1989, Molecular Cloning—A Laboratory Manual, 2nd edition) followed by sucrose gradient fractionation. mRNA in each fraction was determined by in vitro translation and immunoprecipitation.

2. Synthesis of cDNA and Preparation of cDNA Library

Complementary DNA (cDNA) was prepared from mRNA following the Gubler-Hoffman procedure (Gubler and Hoffman, 1983, Gene 25:263–269). The first strand was synthesized in a 50 μl reaction mixture containing 3 μg mRNA, 50 mM Tris-HCl (pH 7.5), 65 mM KCl, 3 mM $MgCl_2$, 10 mM DTT, 0.5 μg oligo(dT), 2.5 μg Actinomycin D, 1 mM each of 4 dNTP's and 2 units of Mudne Leukemia Virus (MLV) reverse transcriptase. The reaction was incubated at 0° C. for 3 minutes, then 20° C. for 5 minutes and 37° C. for 1 hour. Two μl 0.5M EDTA and 5 μl 3M NaCl was added at the end of reaction. The mixture was extracted with phenol/chloroform and precipitated with 2 volumes of ethanol. The second strand was prepared by a repair synthesis reaction using RNase H, DNA polymerase, and DNA ligase. The DNA obtained from first strand synthesis was dissolved in 100 μl repair buffer containing 20 mM Tris-HCl (pH 7.5), 5 mM $MgCl_2$, 10 mM ammonium sulfate, 100 mM KCl, 150 μM β-NAD, 40 μM each of 4 dNTP's, 5 μg BSA, 1 unit *E. coli* RNase H, 20 units DNA polymerase I, and 1 unit *E. coli* DNA ligase. The mixture was incubated at 12° C. for 1 hour and then 1 hour at 20° C. At the end of the reaction, 10 μl of 3M NaCl was added and the mixture was extracted with phenol/chloroform. The DNA was precipitated by adding 2 volumes of ethanol. The cDNA was C-tailed using terminal deoxynucleotidyl transferase (TdT) and dCTP. One ng of C-tailed cDNA was annealed and ligated to 25 ng of G-tailed plasmid pUC19. The ligated DNA was used to transform and prepare a cDNA library in *E. coli*.

3. Preparation of Oligonucleotide Probes

A set of four oligonucleotide probes (FIG. 2, SEQ. ID. NO.:11 ) was derived from the reverse translation of seven amino acids (SEQ. ID. NO.:8) from the peptide C (FIG. 1, SEQ. ID NO.:5), which is near the carboxyl end of the PVA enzyme.

4. Identification of the PVA cDNA Clone and Generation of A Full Length cDNA

The colonies of cDNA library were screened with a degenerate oligonucleotide probe (FIG. 2, SEQ. ID. NO.:11). Colony blots were screened by hybridization to $^{32}P$ end-labeled probes in hybridization buffer (6X NET/10X Denhardts/1% SDS) at 50° C.

The hybridized membrane was washed twice at room temperature for 30 minutes each with 2X NET-0.1% SDS, followed by two 30 minutes washes at 50° C. with 0.5X NET–0.1% SDS. A strongly hybridizing colony (#362) was selected for further study. It contained a 500 bp insert which was used as a probe to rescreen the library. A second clone (#2585) contained a 1.7 kb insert and hybridized strongly to the probe. Comparison of the N-terminal amino acid sequence of the PVA to the translation of the 5' end of the insert indicated that the entire coding region of the mature enzyme except for five amino acids had been cloned (FIG.

Figure 4:
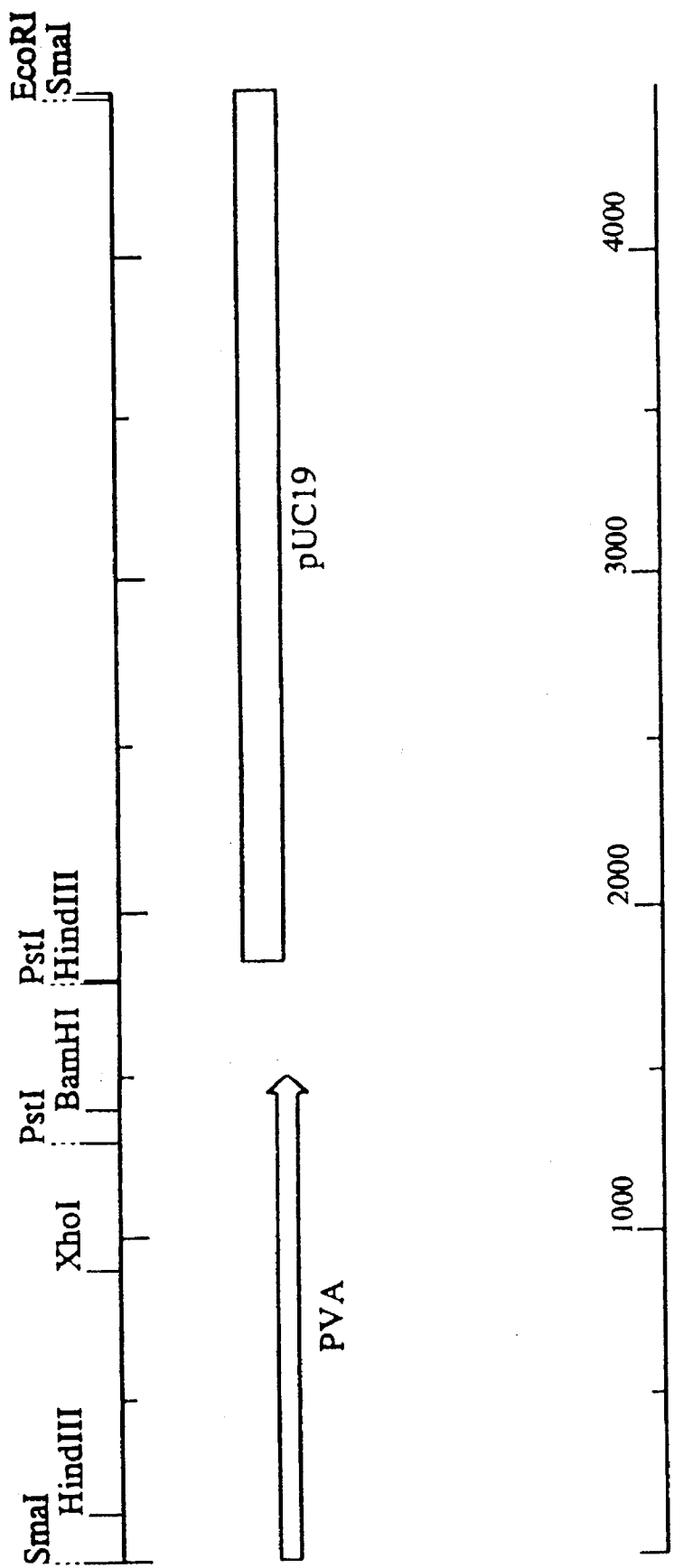
FIG. 4—Schematic representation of 2585-FL.

3). A PstI restriction site was created at the 5' end by site specific mutagenesis to generate #2585-M. A synthetic linker was added to convert #2585-M clone to a full-length cDNA clone, 2585-FL (FIGS. 3 and 4).

5. DNA Sequence Analysis of 2585-FL cDNA Clone

Both strands of the cDNA insert 2585-FL were sequenced by the Maxam-Gilbert method (Maxam and Gilbert, 1977, Proc. Natl. Acad. Sci. U.S.A. 74:560–564). The insert contains a 1521 base pair (bp) open reading frame which can code for a 55,000 dalton protein (FIG. 6). All of the amino acid sequence data from the N-terminus of the intact PVA molecule and cyanogen bromide digested peptide fragments are found in this sequence. The region (base pairs 1348 to 1368, SEQ. ID. NO.:20) corresponding to the 20 mer oligonucleotide probe (SEQ. ID. NO.:11) is underlined in FIG. 6.

EXAMPLE 3

Penicillin V Amidase Genomic DNA Cloning

1. Identification of the Genomic PVA Gene Fragment

High molecular weight chromosomal DNA from *F. oxysporum* strain 435 was digested with several restriction enzymes, electrophoresed through a 0.6% agarose gel in TAE buffer, and transferred to nitrocellulose. A probe prepared from 2585 insert DNA was hybridized to the Southern blot to determine the size of the fragments containing the PVA gene. The gene was found on a ~12 kb EcoRI fragment.

2. Construction of Plasmid pWB19N pBM11/M5 (ATCC 67436) is derived from pBM11 (ATCC 67366) in which a NcoI site present in the neomycin-resistance gene has been removed by site-specific mutagenesis. Plasmid pBM11/M5 DNA was digested with HindIII and SmaI. The 5' protruding ends of the HindIII cut were converted to blunt ends using the Klenow fragment of *E. coli* DNA polymerase I. The DNA mixture was subjected to electrophoresis on a 0.8% preparative agarose gel. The 1.3 kb fragment containing the neomycin-resistance gene was excised from the gel and subjected to electroelution at 100 V for 1 hour at room temperature. The resulting eluate was collected and extracted 3 times with an equal volume of TE-saturated phenol. DNA was recovered from the aqueous phase by ethanol precipitation in the presence of 0.3M NaCl. The recovery of the DNA fragment was analyzed by agarose gel electrophoresis.

The pUC19 plasmid DNA (Yanisch-Perron et al., 1985, Gene, 33:103–119) was cleaved with BspHI and the 5' protruding ends were converted to blunt ends with Klenow fragment. The 1.6 kb fragment (base pair No. 2639 to No. 2686 and No. 1 to No. 1526) containing the polylinker sites and the origin of replication was isolated and ligated to the 1.3 kb neomycin-resistance gene fragment in the presence of ligation buffer (50 mM Tris-HCl, pH 7.6, 10 mM MgCl$_2$, 1 mM ATP, 1 mM DTT, 5% polyethylene glycol-8000) and T4 DNA ligase.

The resultant plasmid, designated pWB19N, was electroporated into *E. coli* DH5α cells. Neomycin resistant colonies were screened for the presence of pWB19N plasmid which has one restored BspHI site at the junction point of the Klenow filled-in HindIII and BspHI sites. The colonies were also screened for ampicillin sensitivity and α-complementation of β-galactosidase activity on X-gal plates. The construction of pWB19N is depicted in FIG. 8.

3. Cloning of the Genomic PVA Gene Fragment

One hundred μg of high molecular weight chromosomal DNA from *F. oxysporum* strain 435 was cleaved with EcoRI. The DNA was electrophoresed through a 0.6% agarose gel in TAE buffer. DNA in the size range of 11.5 kb to 12 kb was excised from the gel and subjected to electroelution at 100V for 1 hour at room temperature. The resulting eluate was collected and extracted 3 times with an equal volume of TE-saturated phenol. DNA was recovered from the aqueous phase by ethanol precipitation in the presence of 0.3M NaCl. The ~12 kb DNA fragment was then cloned into the pWB19N vector to form pF021 (FIG. 5). Restriction analysis of pF021 DNA revealed that the cloned fragment contains the entire PVA gene, with an additional 3.7 kb upstream and 6.8 kb downstream of the PVA coding sequences.

4. DNA Sequence Analysis

The coding region of the genomic clone was also sequenced by the Maxam-Gilbert method (FIG. 7). The cDNA and genomic sequences were identical except for the codon usage at the 5' end where a synthetic linker had been inserted in the cDNA clone. In the genomic clone, an additional 315 bp of sequence information was obtained at the 5' end. This data suggests that the translation of PVA mRNA begins at base 241 of FIG. 7 and that a "pre-PVA" containing a 25 amino acid signal sequence is synthesized and then cleaved to form the secreted form of PVA enzyme.

The transcription start site was determined by S1 mapping (Berk and Sharp, 1977, Cell 12:721–732,; Sambrook et al., 1989, Molecular Cloning—A Laboratory Manual, 2nd edition). It is located at or near base 162. No other potential ATG translation start signals are found between this site and the ATG at base 241.

EXAMPLE 4

PVA Gene Expression in Heterologous Hosts

1. Construction of plasmid pSJC62

Plasmid pES200 (Staben et al., 1989, Fungal Genet. Lett. 36:79–81 ) has the trpC promoter sequence from *Aspergillus nidulans* to direct the transcription of the bacterial hygromycin B-resistance gene. The pES200 DNA was cleaved with EcoRI and ClaI enzymes; the 5' protruding ends were converted to blunt ends with Klenow fragment. The 1250 bp trpC promoter fragment was isolated by agarose gel electrophoresis and recovered by electroelution. Plasmid pUT715 (Jain et al., 1992, Mol. Ge. Genet. 234:489–493) is a promoter probe vector carrying a promoter-less phleomycin-resistance gene from *Streptoalloteichus hindustanus*. The pUT715 DNA was digested with EcoRV and ligated to the 1250 bp trpC promoter fragment. The ligation mixture was transformed into *E. coli* DH5α and the resultant plasmid was designated as pUT715/trpC.

The pUT715/trpc DNA was digested with BamHI and BglII enzymes. The 2.4 kb fragment consisting of the trpC promoter and the phleomycin-resistance gene was isolated after agarose gel electrophoresis. The pWB19N DNA was cleaved with BamHI enzyme and ligated to the 2.4 kb fragment. The resultant plasmid was designated pSJC62 (FIG. 9).

2. Construction of pFO23

The plasmid pFO21 has an insert of a ~12 kb EcoRI fragment from the *F. oxysporum* strain 435 genomic DNA. The pFO21 DNA was cleaved by SalI enzyme and recircularized with T4 DNA ligase. The resultant plasmid pFO23 has a 5.8 kb deletion of the non-coding Fusarium DNA from pFO21 (FIG. 5).

3. Construction of pBMFXPVA6

The pSJC62 DNA was cleaved with EcoRI and XbaI enzymes. The resulting 2.4 kb fragment consisting of the Aspergillus trpC promoter plus the phleomycin-resistance gene was isolated. The pFO23 DNA was digested with EcoRI and XbaI enzymes. The DNA mixture was separated on agarose gel. A 7.9 kb fragment containing the PVA gene was isolated and ligated to the 2.4 kb fragment consisting the Aspergillus trpC promoter and the phleomycin-resistance gene. The resultant plasmid was designated pBMFXPVA6 (FIG. 10).

4. Construction of pBMFXPVA7

The pBMFXPVA6 DNA was cleaved with NcoI and XbaI enzymes. The cohesive ends were converted to blunt ends with Klenow fragment. The DNA mixture was separated on an agarose gel and 4.3 kb fragment containing the PVA gene was isolated. The pBMFXPVA6 DNA was cleaved with XbaI and treated with Klenow fragment. The linearized pBMFXPVA6 DNA was ligated to the 4.3 kb PVA gene fragment to form pBMFXPVA7 (FIG. 11).

5. PVA Gene Expression in Heterologous Host

Recombinant plasmid pBMFXPVA6 was derived from pFO23 (FIG. 5) with the addition of a phleomycin-resistance gene which is regulated by the trpC promoter of *Aspergillus nidulans* (FIG. 10). Recombinant plasmid pBMFXPVA7 was derived from pBMFXPVA6 with an addition of a second copy of the PVA gene (FIG. 11). These recombinant plasmids were introduced into ATCC 16322 strain (*F. oxysporum* f. sp. lycopersici), which is a heterologous host (i.e., a different subspecies of *F. oxysporum*) of the PVA gene, via polyethylene glycol mediated protoplast transformation (Powell and Kistler, 1990, J. Bactedol -continued ATACGCGTC (SEQ. ID. NO.:25)
MluI site The generation of the MluI site allows the removal of the coding region of the PVA gene by MluI and BamHI cleavage and the replacement with a coding sequence of a gene to be expressed under the PVA promoter control. A 15 mer mutagenic oligonucleotide (GGCACTATACGCGTC SEQ. ID. NO.:26) was synthesized.

The construction of pF020-P was diagrammed in FIG. 13. Two μg of pF020 was digested with XmaI, followed by treatment with bacterial alkaline phosphatase (BAP) to prevent self-ligation of the resulting fragment I. Two μg of pF020 was cleaved with EcoRI and SphI to remove the mutation target region (e.g., the upstream region of the PVA gene). The resulting 5 kb fragment (fragment II) was gel-purified. Equal molar amounts of fragments I and II were mixed with a 200 fold molar excess of the 15 mer mutagenic oligonucleotide. The mixture was incubated at 100° C. for 3 minutes in order to completely denature the DNA fragments in the mixture. After the denaturation, mixture was gradually cooled in a step-wise manner to allow the denatured DNA fragment to reanneal. During this reannealing procedure, two new species of DNAs, DNA-a and DNA-b were formed in addition to the original fragments I and II. As shown in FIG. 13, the 15 mer mutagenic oligonucleotide hybridized with only one of the two species of circular DNAs to form the heteroduplex, since the oligonucleotide was complementary to only one of the two strans of the target region. The DNAs were incubated with the Klenow fragment, T4 DNA ligase and four dNTP's. This treatment convened the open circular DNAs to closed circular DNAs. After the reaction, the mixture was used for transformation of *E. coli* DH5α. Plasmids DNAs of transformants were screened by MluI clavage analysis. Plasmid pF020-P was identified for the creation of a MluI site.

3. Construction of pBMPVA-P

Since the pF020-P has two BamHI sites which prevent the use of this expression vector, the BamHI site from the region of the pUC19 vector needs to be removed. pF020-P was treated with a limited amount of BamHI enzyme to generate a partial cleavage condition and then cleaved with EcoRI. The 5' protruding ends were filled in with the Klenow fragment. A 6.3 kb fragment was gel-purified, ligated with T4 DNA ligase and transformed into DH5α. The resulting plasmid pBMPVA-P (FIG. 14) can be used as an expression vector to insert a coding sequence of the desired gene at the MluI/BamHI sites under the PVA promoter control.

4. Construction of pF020-M

A SmaI site was generated at the junction of the PVA secretion signal sequence and mature PVA protein (amino acid No. 24–25, SEQ. ID. NO.:22).

AACAAA/GGCAAC (SEQ. ID. NO.:27)

N K G N (SEQ. ID. NO.:28)

| site-specific mutagenesis
↓

AACCCC/GGGAAC (SEQ. ID. NO.:29)
SmaI site

The creation of the SmaI sites allows the insertion of a coding sequence after the PVA secretion signal sequence and thus will allow secretion of the expressed protein. A 28 mer mutagenic oligonucleotide (GCAGCTCCCAACCCCGG-GAACGATGATT, SEQ. ID. NO.:30) was synthesized.

The construction of pF020-M was shown in FIG. 15. The process was similar to the construction of pF020-P. Plasmid pF020 was cleaved with XmaI, followed by BAP treatment to generate fragment I. pF020 was then digested with SphI and HindIII to remove the target region and generate a 6 kb fragment II. The conditions of heteroduplex formation and DNA extension was similar to the pF020-P construction. Plamids DNAs of transformants were screened for the creation of an additional SmaI site.

5. Construction of pBMPVA-M

Plasmid pF020-M has two BamHI and two SmaI sites which prevent the use of this vector. The extra BamHI and SmaI sites from the region of pUC19 need to be removed. pF020-M was partially cleaved with BamHI and then cleaved with EcoRI. The cohesive ends were filled with the Klenow fragment. A 6.3 kb fragment was gel-purified, ligated and transformed into *E. coli* DH5α. The resulting plasmid pBMPVA-M (FIG. 16) can be used as a secretable expression vector to insert a coding sequence of the desired gene at the SmaI/BamHI sites under the PVA promoter control.

EXAMPLE 6

Expression of the D-Amino Acid Oxidase Gene by the PVA Expression Vectors

A D-amino acid oxidase gene which was cloned from *Trigonopsis variabilis* was used as an example of a foreign gene to be expressed by the Fusarium PVA expression vectors.

1. Expression of the D-Amino Acid Oxidase Gene By pBMPVA-P

The D-Amino acid oxidase (DAAO) gene of *Trigonopsis variabilis* was cloned by Bristol-Myers Squibb scientists. The DNA sequence analysis indicated that a 38 bp intron exists near the 5' end of the coding sequence. Oligonucleotide directed site-specific mutagenesis method was used to remove the intron and create a NcoI site at the translation start site of the DAAO gene. Therefore, the DAAO coding sequence plus a 700 bp 3' non-transcriptional region can be purified as a 2.1 kb NcoI/BamHI fragment.

Plasmid pBMPVA-P DNA was treated with MluI cleavage and the cohesive ends were filled in with the Klenow fragment. The DNA was then cleaved with BamHI. A 4.7 kb fragment containing the PVA promoter region was gel-purified. The DDAO gene fragment was ligated with the 2.1 kb NcoI-Klenow/BamHI fragment of DAAO ene to generate plasmid pBMPVA-P/DAA01. A 3.4 kb PVA promoter/DAAO gene fusion fragment was prepared by NdeI cleavage and Klenow filled-in of plasmid pBMPVA-P/DAA01 and gel-purified. The fragment was inserted into pSJC62 DNA and the Klenow filled-in XbaI site. The resulting plasmid was designated as pBMPVA-P/DAA02. The entire construction scheme is depicted in FIG. 17.

The pBMPVA-P/DAA02 DNA was introduced into ATCC 16322 strain by polyethylene glycol mediated protoplast transformation. Transformants were selected from its resistance to phleomycin. Several transformants were grown in PVA production medium and assayed for D-amino acid oxidase activity. The results indicated that the D-amino acid oxidase gene was expressed in ATCC 16322 transformants at a level of 0.2–0.8 IU/ml.

2. Expression of the D-Amino Acid Oxidase Gene by pBMPVA-M

Plasmid pBMPVA-M DNA was cleaved with SmaI and BamHI enzymes. A 4.8 kb fragment containing the PVA promoter region as well as the PVA secretable signal sequence was gel-purified. The DAAO gene fragment was prepared by NcoI cleavage plus mung bean nuclease treatment to remove the 5' cohesive ends and maintain a proper reading frame of the DAAO gene, and then BamHI digestion to generate a 2.1 kb fragment. The 4.8 kb PVA promoter/signal sequence fragment was ligated to the 2.1 kb DAAO gene fragment to generate plasmid pBMPVA-M/DAA 03. The pBMPVA-M/DAA03 DNA was cleaved with NdeI and the 5' cohesive ends were filled in with the Klenow fragment. The 3.5 kb PVA promoter-signal sequence/DAAO gene fusion fragment was purified and inserted into pSJC62 DNA at Klenow filled-in XbaI site. The resulting plasmid was designated as pBMPVA-M/DAA04 (FIG. 18).

The pBMPVA-M/DAA04 DNA was transformed into ATCC 16322 strain. Several phleomycin-resistan transformants were assayed for D-amino acid oxidase activity. Unfortunately, none of the transformants showed D-amino acid oxidase activity. The failure of the expression of the D-amino acid oxidase gene by pBMPVA-M vector may be due to the intracellular nature of the D-amino acid oxidase enzyme. It is widely recognized that genes encoding intracellular protein can not be expressed and translocated extracellularly by a secretable expression system (Model and Russel, 1990, Cell 61:739–741). Even if the gene is expressed intracellularly, the attachment of the PVA signal sequence may inactivate the D-amino acid oxidase activity. Therefore, the pBMPVA-M vector should still be useful for expression of other secretable protein genes.

---

What we claim is:

1. An isolated nucleic acid molecule having a sequence coding for the amino acid sequence of SEQ. ID. NOS.: 19 or 22.

2. An isolated nucleic acid molecule having a sequence complementary to a nucleic acid sequence coding for the amino acid sequence of SEQ. ID. NOS.:19 or 22.

3. An isolated nucleic acid molecule having a sequence capable of hybridizing under stringent conditions to a nucleic acid having a sequence complementary to a nucleic acid sequence coding for the amino acid sequence of SEQ. ID. NOS.:19 or 22.

4. The nucleic acid molecule of claim 1 which is a DNA molecule.

5. The nucleic acid molecule of claim 2 which is a DNA molecule.

6. The nucleic acid molecule of claim 3 which is a DNA molecule.

7. An isolated DNA molecule having a sequence coding for the amino acid sequence of SEQ. ID. NO.:19.

8. An isolated DNA molecule having a sequence capable of hybridizing under stringent conditions to a nucleic acid having a sequence complementary to a nucleic acid sequence coding for the amino acid sequence of SEQ. ID. NO.:19.

9. An isolated DNA molecule having a sequence coding for the amino acid sequence of SEQ. ID. NO.:22.

10. An isolated DNA molecule having a sequence capable of hybridizing under stringent conditions to a nucleic acid having a sequence complementary to a nucleic acid sequence coding for the amino acid sequence of SEQ. ID. NO.:22.

11. An isolated DNA molecule having the nucleotide sequence of SEQ. ID. NO.:18.

12. An isolated DNA molecule having the nucleotide sequence of SEQ. ID. NO.:21.

13. An isolated DNA molecule having the nucleotide sequence of SEQ. ID. NO.: 11.

14. An isolated DNA molecule having the nucleotide sequence of SEQ. ID. NO.: 23.

15. An isolated DNA molecule having the nucleotide sequence of SEQ. ID. NOS.: 14, 15, 16, or 17.

16. An isolated DNA molecule having the nucleotide sequence of SEQ. ID. NOS.:9 or 10.

17. An isolated DNA molecule having the nucleotide sequence of SEQ. ID. NOS.:26 or 30.

18. An isolated polypeptide having the amino acid sequence of SEQ. ID. NOS.:1, 2, 3, 4, 5, 6, 8, or 12.

19. The polypeptide of claim 18 having the amino acid sequence of SEQ. ID. NOS.:1 or 12.

20. An expression vector comprising a nucleic acid sequence coding for the amino acid sequence of SEQ. ID. NOS.:19 or 22.

21. The expression vector of claim 20 comprising a DNA sequence coding for the amino acid sequence of SEQ. ID. NO.:19.

22. The expression vector of claim 20 comprising a DNA sequence coding for the amino acid sequence of SEQ. ID. NO.:22.

23. The expression vector of claim 20 further comprising an origin of replication, a promoter, and a transcription termination sequence.

24. The expression vector of claim 23 further comprising a selectable marker sequence.

25. The expression vector of claim 24 wherein the selectable marker is phleomycin resistance.

26. The expression vector of claim 23 which is capable of integrating into fungal chromosomes.

27. The expression vector of claim 20 having the DNA sequence of SEQ. ID. NOS.:18 or 21.

28. The expression vector of claim 20 which is a plasmid.

29. An expression vector comprising a promoter having the DNA sequence of SEQ. ID. NO.:23.

30. The expression vector of claim 29 further comprising an origin of replication, DNA coding for a structural protein, and a transcription termination sequence.

31. The expression vector of claim 30 wherein the DNA coding for a structural protein codes for penicillin V amidohydrolase (PVA).

32. The expression vector of claim 30 further comprising a selectable marker sequence.

33. The expression vector of claim 32 wherein the selectable marker is phleomycin resistance.

34. The expression vector of claim 30 which is capable of integrating into fungal chromosomes.

35. An expression vector having the designation pBM-FXPVA6.

36. An expression vector having the designation pBM-FXPVA7.

37. An expression vector having the designation pBMPVA-P.

38. An expression vector having the designation pBMPVA-M.

39. A host cell containing the expression vector of claim 20.

40. A host cell containing the expression vector of claim 23.

41. A host cell containing the expression vector of claim 25.

42. A host cell containing the expression vector of claim 26.

43. A host cell containing the expression vector of claim 27.

44. A host cell containing the expression vector of claim 28.

45. A host cell containing the expression vector of claim 29.

46. A host cell containing the expression vector of claim 30.

47. A host cell containing the expression vector of claim 31.

48. A host cell containing the expression vector of claim 32.

49. A host cell containing the expression vector of claim 33.

50. A host cell containing the expression vector of claim 34.

51. A host cell containing the expression vector of claim 35.

52. A host cell containing the expression vector of claim 36.

53. A host cell containing the expression vector of claim 37.

54. A host cell containing the expression vector of claim 38.

55. The host cell of claim 39 which is eukaryotic.

56. The host cell of claim 45 which is eukaryotic.

57. The host cell of claim 39 which is a Fusarium species.

58. The host cell of claim 45 which is a Fusarium species.

59. The host cell of claim 39 which is *Fusarium oxysporum.*

60. The host cell of claim 45 which is *Fusarium oxysporum.*

61. The host cell of claim 51 which is *Fusarium oxysporum.*

62. The host cell of claim 52 which is *Fusarium oxysporum.*

63. The host cell of claim 53 which is *Fusarium oxysporum.*

64. The host cell of claim 54 which is *Fusarium oxysporum.*

65. A biologically pure culture of *Escherichia coil* ATCC 69720.

66. A biologically pure culture of *Escherichia coil* ATCC 69721.

67. A biologically pure culture of *Escherichia coil* ATCC 69772.

68. A method for producing a polypeptide having the amino acid sequence of SEQ. ID. NOS.:19 or 22 comprising culturing the host cell of claim 39 under conditions resulting in expression of the polypeptide.

69. The method of claim 68 wherein expression is induced by culturing in the presence of phenoxyacetate.

70. A method for producing a polypeptide comprising culturing the host cell of claim 45 under conditions resulting in expression of the polypeptide.

71. The method of claim 70 wherein expression is induced by culturing in the presence of phenoxyacetate.

* * * * *

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Fusarium oxysporum ( i x ) FEATURE:
        ( A ) NAME/KEY: Peptide
        ( B ) LOCATION: 7
        ( D ) OTHER INFORMATION: /note="Amino acid 7 can be ala or
            lys"

( i x ) FEATURE:
        ( A ) NAME/KEY: Peptide
        ( B ) LOCATION: 22
        ( D ) OTHER INFORMATION: /note="Amino acid 22 can be Thr or
            Val"

( x i ) SEQUENCE DESCRIPTION: SEQ ID NO:1:

```
Gly Asn Asp Asp Phe Ala Xaa Lys Xaa Ala Ser Leu Lys Lys Ser Leu
 1               5                  10                      15

Lys Leu Pro Gly Thr Xaa Val Tyr Phe Thr Gln His Val
             20                  25
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
 ( A ) NAME/KEY: Peptide
 ( B ) LOCATION: 4
 ( D ) OTHER INFORMATION: /note="amino acid 4 can be ser or
  pro"

( i x ) FEATURE:
 ( A ) NAME/KEY: Peptide
 ( B ) LOCATION: 7
 ( D ) OTHER INFORMATION: /note="amino acid 7 can be ala or
  leu"

( i x ) FEATURE:
 ( A ) NAME/KEY: Peptide
 ( B ) LOCATION: 8
 ( D ) OTHER INFORMATION: /note="amino acid 8 can be asp or
  glu"

( i x ) FEATURE:
 ( A ) NAME/KEY: Peptide
 ( B ) LOCATION: 12
 ( D ) OTHER INFORMATION: /note="amino acid 12 can be tyr or
  arg"

( x i ) SEQUENCE DESCRIPTION: SEQ ID NO:2:

Gly Leu Asn Xaa Ser Gln Xaa Xaa Gln Phe Tyr Xaa
1     5        10

( 2 ) INFORMATION FOR SEQ ID NO:3:

( i ) SEQUENCE CHARACTERISTICS:
  ( A ) LENGTH: 12 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Peptide
  ( B ) LOCATION: 8
  ( D ) OTHER INFORMATION: /note="amino acid 8 can be ser or
   lys"

( x i ) SEQUENCE DESCRIPTION: SEQ ID NO:3:

Leu Val Lys Thr Gly Pro Ala Xaa Xaa Val Ser Ile
1     5        10

( 2 ) INFORMATION FOR SEQ ID NO:4:

( i ) SEQUENCE CHARACTERISTICS:
  ( A ) LENGTH: 10 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Peptide
  ( B ) LOCATION: 8
  ( D ) OTHER INFORMATION: /note="amino acid 8 can be ser or
   lys"

( x i ) SEQUENCE DESCRIPTION: SEQ ID NO:4:

Gly Asn Asp Asp Phe Ala Ala Xaa Xaa Ala
1     5        10

( 2 ) INFORMATION FOR SEQ ID NO:5:

( i ) SEQUENCE CHARACTERISTICS:
  ( A ) LENGTH: 20 amino acids
  ( B ) TYPE: amino acid
  ( C ) STRANDEDNESS:

( D ) TOPOLOGY: linear ( i i ) MOLECULE TYPE: peptide ( i x ) FEATURE:
            ( A ) NAME/KEY: Peptide
            ( B ) LOCATION: 3
            ( D ) OTHER INFORMATION: /note="amino acid 3 can be asn or
                    lys"

( i x ) FEATURE:
            ( A ) NAME/KEY: Peptide
            ( B ) LOCATION: 13
            ( D ) OTHER INFORMATION: /note="amino acid 13 can be ile or
                    arg"

( x i ) SEQUENCE DESCRIPTION: SEQ ID NO:5:

Gly  Xaa  Xaa  Thr  Ala  Asp  Thr  Asn  Val  Leu  Leu  Ala  Xaa  Val  Lys  Trp
1                  5                            10                           15

Val  Glu  Glu  Gly
              20

( 2 ) INFORMATION FOR SEQ ID NO:6:

( i ) SEQUENCE CHARACTERISTICS:
            ( A ) LENGTH: 25 amino acids
            ( B ) TYPE: amino acid
            ( C ) STRANDEDNESS:
            ( D ) TOPOLOGY: linear ( i i ) MOLECULE TYPE: peptide ( i x ) FEATURE:
            ( A ) NAME/KEY: Peptide
            ( B ) LOCATION: 16
            ( D ) OTHER INFORMATION: /note="amino acid 16 can be asn or
                    ser"

( i x ) FEATURE:
            ( A ) NAME/KEY: Peptide
            ( B ) LOCATION: 21
            ( D ) OTHER INFORMATION: /note="amino acid 21 can be asn or
                    his"

( i x ) FEATURE:
            ( A ) NAME/KEY: Peptide
            ( B ) LOCATION: 23
            ( D ) OTHER INFORMATION: /note="amino acid 23 can be val or
                    ser"

( i x ) FEATURE:
            ( A ) NAME/KEY: Peptide
            ( B ) LOCATION: 25
            ( D ) OTHER INFORMATION: /note="amino acid 25 can be thr or
                    arg"

( x i ) SEQUENCE DESCRIPTION: SEQ ID NO:6:

Ile  His  Trp  Ser  Gly  Leu  Glu  Asp  Gly  Leu  Ile  Ser  Ala  Glu  Asn  Xaa
1                  5                            10                           15

Asp  Tyr  Tyr  Asn  Xaa  Val  Xaa  Ser  Xaa
              20                      25

( 2 ) INFORMATION FOR SEQ ID NO:7:

( i ) SEQUENCE CHARACTERISTICS:
            ( A ) LENGTH: 4 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:7:

Pro Tyr Asn Asp
1

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

Val Lys Trp Val Glu Glu Gly
1               5

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GTNAARTGGG TNGARGARGG    20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CCYTCYTCNA CCCAYTTNAC    20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CCYTCYTCNT CGGAYTTNAC    20

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:12:

Gly Asn Asp Asp Phe Ala Ala Lys Cys Ala ( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

Val Ala Lys Cys Ala
1             5

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TTTTTTTGT AGCGAAATGC GCC     23

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TTTTTCTGC AGCGAAATGC GCC     23

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CCCGGGAACG ACGACTTTGC AGCGAAATGC GCC     33

( 2 ) INFORMATION FOR SEQ ID NO:17:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GGCGCATTTC GCTGCAAAGT CGTCGTTCCC GGG     33

( 2 ) INFORMATION FOR SEQ ID NO:18:

5,516,679

31

32

-continued ( i ) SEQUENCE CHARACTERISTICS:
    ( A ) LENGTH: 1767 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..1521

( x i ) SEQUENCE DESCRIPTION: SEQ ID NO:18:

| | | | | | | | | | | | | | | | | |
|---|---|---|---|---|---|---|---|---|---|---|---|---|---|---|---|---|
| GGC | AAC | GAT | GAT | TTT | GCC | GCG | AAA | TGC | GCC | AGC | CTC | AAG | AAG | TCG | CTC | 48 |
| Gly | Asn | Asp | Asp | Phe | Ala | Ala | Lys | Cys | Ala | Ser | Leu | Lys | Lys | Ser | Leu | |
| 1 | | | | 5 | | | | | 10 | | | | | 15 | | |
| AAA | CTC | CCC | GGC | ACC | ACC | GTA | TAC | TTC | ACC | CAG | CAT | GTC | TCG | GCT | GGT | 96 |
| Lys | Leu | Pro | Gly | Thr | Thr | Val | Tyr | Phe | Thr | Gln | His | Val | Ser | Ala | Gly | |
| | | | 20 | | | | | 25 | | | | | 30 | | | |
| ACC | AAC | ATC | ACT | TTC | CCC | GAT | AAT | CAC | CCG | ACC | TGC | GGT | CCT | AAC | TAT | 144 |
| Thr | Asn | Ile | Thr | Phe | Pro | Asp | Asn | His | Pro | Thr | Cys | Gly | Pro | Asn | Tyr | |
| | | 35 | | | | | 40 | | | | | 45 | | | | |
| CAG | GTT | ACG | GAC | GTT | GAG | GTC | TGC | CGC | GTG | GCC | ATG | TTA | GTC | AAG | ACG | 192 |
| Gln | Val | Thr | Asp | Val | Glu | Val | Cys | Arg | Val | Ala | Met | Leu | Val | Lys | Thr | |
| | 50 | | | | | 55 | | | | | 60 | | | | | |
| GGA | CCC | GCC | TCA | AAC | GTT | AGC | ATC | GAA | GCT | TGG | CTT | CCC | TTG | AAC | TGG | 240 |
| Gly | Pro | Ala | Ser | Asn | Val | Ser | Ile | Glu | Ala | Trp | Leu | Pro | Leu | Asn | Trp | |
| 65 | | | | | 70 | | | | | 75 | | | | | 80 | |
| ACA | GGT | CGG | TTC | TTA | GGA | ACT | GGC | AAT | GGT | GGA | TTA | GCT | GGC | TGT | ATG | 288 |
| Thr | Gly | Arg | Phe | Leu | Gly | Thr | Gly | Asn | Gly | Gly | Leu | Ala | Gly | Cys | Met | |
| | | | | 85 | | | | | 90 | | | | | 95 | | |
| CCC | TAC | AAC | GAT | ATG | GCG | TAC | GGC | AAC | AGT | TTC | GGC | TTC | GCC | AGC | GTT | 336 |
| Pro | Tyr | Asn | Asp | Met | Ala | Tyr | Gly | Asn | Ser | Phe | Gly | Phe | Ala | Ser | Val | |
| | | | 100 | | | | | 105 | | | | | 110 | | | |
| GGC | ACG | AAC | AAC | GGA | CAT | AAC | GGA | ACC | TCA | GGC | CTA | CCC | ATG | TAC | CGC | 384 |
| Gly | Thr | Asn | Asn | Gly | His | Asn | Gly | Thr | Ser | Gly | Leu | Pro | Met | Tyr | Arg | |
| | | 115 | | | | | 120 | | | | | 125 | | | | |
| AAC | CCA | GGC | GTG | GTT | GAG | GAC | TTT | GCC | TAT | CGT | GCG | GTG | CAC | GCT | GGT | 432 |
| Asn | Pro | Gly | Val | Val | Glu | Asp | Phe | Ala | Tyr | Arg | Ala | Val | His | Ala | Gly | |
| | 130 | | | | | 135 | | | | | 140 | | | | | |
| GCT | GTT | ATC | GGA | AAG | AAG | ATC | ACC | CAG | GGC | TTT | TAC | GGC | AAG | AAG | TTC | 480 |
| Ala | Val | Ile | Gly | Lys | Lys | Ile | Thr | Gln | Gly | Phe | Tyr | Gly | Lys | Lys | Phe | |
| 145 | | | | | 150 | | | | | 155 | | | | | 160 | |
| AAG | TCC | TAC | TTT | CTC | GGC | TGC | TCG | ACA | GGA | GGA | CGT | CAA | GCA | ATG | AAG | 528 |
| Lys | Ser | Tyr | Phe | Leu | Gly | Cys | Ser | Thr | Gly | Gly | Arg | Gln | Ala | Met | Lys | |
| | | | | 165 | | | | | 170 | | | | | 175 | | |
| TTG | GCA | CAG | AGC | TTC | CCC | GAG | GAT | TAC | GAT | GGC | TAT | GTG | GCA | GGT | GCT | 576 |
| Leu | Ala | Gln | Ser | Phe | Pro | Glu | Asp | Tyr | Asp | Gly | Tyr | Val | Ala | Gly | Ala | |
| | | | 180 | | | | | 185 | | | | | 190 | | | |
| CCG | GCT | ATG | CGC | TGG | AAC | GGT | CTT | CAG | GCA | CGC | TCT | GGA | AGT | TTC | TGG | 624 |
| Pro | Ala | Met | Arg | Trp | Asn | Gly | Leu | Gln | Ala | Arg | Ser | Gly | Ser | Phe | Trp | |
| | | 195 | | | | | 200 | | | | | 205 | | | | |
| GGC | ATC | ACC | GGC | CCC | CCT | GGA | GCT | CCT | GGC | CAT | GTG | ACT | CCA | GAC | GAG | 672 |
| Gly | Ile | Thr | Gly | Pro | Pro | Gly | Ala | Pro | Gly | His | Val | Thr | Pro | Asp | Glu | |
| | | 210 | | | | | 215 | | | | | 220 | | | | |
| TGG | GAA | ATG | GTG | CAC | AAG | AGC | GTC | CTG | ACT | CAG | TGC | GAC | GAG | CCC | ATT | 720 |
| Trp | Glu | Met | Val | His | Lys | Ser | Val | Leu | Thr | Gln | Cys | Asp | Glu | Pro | Ile | |
| 225 | | | | | 230 | | | | | 235 | | | | | 240 | |
| GAT | GGC | GTC | GAT | GAC | GGC | GTG | CTT | GAG | GAC | CCC | ACC | CTC | TGT | CAG | TAC | 768 |
| Asp | Gly | Val | Asp | Asp | Gly | Val | Leu | Glu | Asp | Pro | Thr | Leu | Cys | Gln | Tyr | |
| | | | | 245 | | | | | 250 | | | | | 255 | | |
| CGC | CCT | GAG | GCT | CTC | ATC | TGC | GGT | AAG | GGC | CAG | ACC | GAG | AAT | TGC | CTG | 816 |

```
Arg  Pro  Glu  Ala  Leu  Ile  Cys  Gly  Lys  Gly  Gln  Thr  Glu  Asn  Cys  Leu
          260                 265                      270

ACC  AAG  GCC  AAG  ATT  GAG  ACG  GTC  CGC  AAA  GTC  TTT  TCT  CCC  CTA  TAC        864
Thr  Lys  Ala  Lys  Ile  Glu  Thr  Val  Arg  Lys  Val  Phe  Ser  Pro  Leu  Tyr
          275                 280                      285

ACC  ACG  AAT  GAG  ACA  TAC  GTC  TAC  CCT  CGA  GCG  GTT  CCT  GGT  GCT  AAC        912
Thr  Thr  Asn  Glu  Thr  Tyr  Val  Tyr  Pro  Arg  Ala  Val  Pro  Gly  Ala  Asn
          290                 295                      300

GCT  CTC  TTT  AAC  TTT  GTT  GTC  GCC  GAG  ACA  CCA  TTC  GTT  TAC  TCC  ACA        960
Ala  Leu  Phe  Asn  Phe  Val  Val  Ala  Glu  Thr  Pro  Phe  Val  Tyr  Ser  Thr
305                      310                      315                      320

GAA  TGG  TAC  CAG  TAT  GTC  ATC  TGG  GAA  GAC  CCT  GAG  TGG  AAT  CCT  GAC       1008
Glu  Trp  Tyr  Gln  Tyr  Val  Ile  Trp  Glu  Asp  Pro  Glu  Trp  Asn  Pro  Asp
                    325                 330                      335

ACT  ATT  GGG  CCC  AAG  GAC  TAT  GAT  AGA  GGT  GCC  GAG  ATG  AAC  CCC  TAT       1056
Thr  Ile  Gly  Pro  Lys  Asp  Tyr  Asp  Arg  Gly  Ala  Glu  Met  Asn  Pro  Tyr
               340                      345                      350

GAC  ATT  GAG  ACT  TGG  GAG  GGA  GAC  CTG  TCT  AAG  TTC  CGC  AAG  CGT  GGC       1104
Asp  Ile  Glu  Thr  Trp  Glu  Gly  Asp  Leu  Ser  Lys  Phe  Arg  Lys  Arg  Gly
               355                      360                      365

AAC  AAG  ATG  ATT  CAC  TGG  CAC  GGC  CTT  CAG  GAC  GGA  CTC  ATC  AGC  GCC       1152
Asn  Lys  Met  Ile  His  Trp  His  Gly  Leu  Gln  Asp  Gly  Leu  Ile  Ser  Ala
          370                 375                      380

GAG  AAC  TCA  GAC  GAT  TAT  TAT  AAT  CAC  GTG  TCT  CGA  ACA  ATG  GGC  CTC       1200
Glu  Asn  Ser  Asp  Asp  Tyr  Tyr  Asn  His  Val  Ser  Arg  Thr  Met  Gly  Leu
385                      390                      395                      400

AAT  AGT  AGC  CAG  CTG  GAC  CAG  TTT  TAT  AGG  TTC  TTC  CGC  GTC  AGT  GGG       1248
Asn  Ser  Ser  Gln  Leu  Asp  Gln  Phe  Tyr  Arg  Phe  Phe  Arg  Val  Ser  Gly
                    405                 410                      415

TGT  GGC  CAT  TGC  AGC  GCC  GGA  GAC  GGG  GCT  TCT  CGC  ATT  GGA  AAC  AAC       1296
Cys  Gly  His  Cys  Ser  Ala  Gly  Asp  Gly  Ala  Ser  Arg  Ile  Gly  Asn  Asn
               420                      425                      430

GCC  GGA  AAC  ATG  GGC  GGC  AAG  ACG  GCA  GAT  ACT  AAT  GTG  CTT  CTG  GCT       1344
Ala  Gly  Asn  Met  Gly  Gly  Lys  Thr  Ala  Asp  Thr  Asn  Val  Leu  Leu  Ala
          435                 440                      445

ATT  GTG  AAA  TGG  GTC  GAG  GAA  GGC  GTT  GCG  CCA  GAA  ACG  ATT  GGG  GGC       1392
Ile  Val  Lys  Trp  Val  Glu  Glu  Gly  Val  Ala  Pro  Glu  Thr  Ile  Gly  Gly
450                      455                      460

TAC  AAG  AAC  GTC  GGC  GGA  ACT  GCA  GAT  GGC  GCT  TTT  GAC  TAT  GAG  CGT       1440
Tyr  Lys  Asn  Val  Gly  Gly  Thr  Ala  Asp  Gly  Ala  Phe  Asp  Tyr  Glu  Arg
465                      470                      475                      480

AGG  CAT  TGC  CGA  TAC  CCA  CAC  CGC  AAT  GTC  TGG  GAC  GGG  AAG  GGG  AAT       1488
Arg  His  Cys  Arg  Tyr  Pro  His  Arg  Asn  Val  Trp  Asp  Gly  Lys  Gly  Asn
                    485                 490                      495

GTG  AAG  GAT  CCC  GAT  AGC  TGG  AAC  TGT  AAG  ATC  TGAGGTGTGG  CCCTAGGCTT       1541
Val  Lys  Asp  Pro  Asp  Ser  Trp  Asn  Cys  Lys  Ile
               500                      505

TTGTGGCTGT  CGTTAGGTGG  CATACGTATA  TAAGAGGATC  ACTGTGAACA  TGCTTTATGT              1601

TGTGCAAGAA  TTGATTGAGA  ATCAGATTGA  GCTTGCAGAG  CCAAGGCAAA  TAGACCCAAC              1661

TGTTGACGAG  ATCTTGGCCG  AAGGTAGAGG  CAACGGGGAG  AGAGACCATG  GAAGACAAGG              1721

CGTAGAAAAT  GGCCGGGGAA  GACGGAAAAA  AAAAACCCCC  CCCCCC                             1767
```

( 2 ) INFORMATION FOR SEQ ID NO:19:

( i ) SEQUENCE CHARACTERISTICS:
        ( A ) LENGTH: 507 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | |
|---|---|---|---|---|---|---|---|---|---|---|---|---|---|---|
| Gly | Asn | Asp | Asp | Phe | Ala | Ala | Lys | Cys | Ala | Ser | Leu | Lys | Lys | Ser | Leu |
| 1 | | | | 5 | | | | | 10 | | | | | 15 | |
| Lys | Leu | Pro | Gly | Thr | Thr | Val | Tyr | Phe | Thr | Gln | His | Val | Ser | Ala | Gly |
| | | | 20 | | | | | 25 | | | | | 30 | | |
| Thr | Asn | Ile | Thr | Phe | Pro | Asp | Asn | His | Pro | Thr | Cys | Gly | Pro | Asn | Tyr |
| | | 35 | | | | | 40 | | | | | 45 | | | |
| Gln | Val | Thr | Asp | Val | Glu | Val | Cys | Arg | Val | Ala | Met | Leu | Val | Lys | Thr |
| | 50 | | | | | 55 | | | | | 60 | | | | |
| Gly | Pro | Ala | Ser | Asn | Val | Ser | Ile | Glu | Ala | Trp | Leu | Pro | Leu | Asn | Trp |
| 65 | | | | | 70 | | | | | 75 | | | | | 80 |
| Thr | Gly | Arg | Phe | Leu | Gly | Thr | Gly | Asn | Gly | Gly | Leu | Ala | Gly | Cys | Met |
| | | | | 85 | | | | | 90 | | | | | 95 | |
| Pro | Tyr | Asn | Asp | Met | Ala | Tyr | Gly | Asn | Ser | Phe | Gly | Phe | Ala | Ser | Val |
| | | | 100 | | | | | 105 | | | | | 110 | | |
| Gly | Thr | Asn | Asn | Gly | His | Asn | Gly | Thr | Ser | Gly | Leu | Pro | Met | Tyr | Arg |
| | | 115 | | | | | 120 | | | | | 125 | | | |
| Asn | Pro | Gly | Val | Val | Glu | Asp | Phe | Ala | Tyr | Arg | Ala | Val | His | Ala | Gly |
| | 130 | | | | | 135 | | | | | 140 | | | | |
| Ala | Val | Ile | Gly | Lys | Lys | Ile | Thr | Gln | Gly | Phe | Tyr | Gly | Lys | Lys | Phe |
| 145 | | | | | 150 | | | | | 155 | | | | | 160 |
| Lys | Ser | Tyr | Phe | Leu | Gly | Cys | Ser | Thr | Gly | Gly | Arg | Gln | Ala | Met | Lys |
| | | | | 165 | | | | | 170 | | | | | 175 | |
| Leu | Ala | Gln | Ser | Phe | Pro | Glu | Asp | Tyr | Asp | Gly | Tyr | Val | Ala | Gly | Ala |
| | | | 180 | | | | | 185 | | | | | 190 | | |
| Pro | Ala | Met | Arg | Trp | Asn | Gly | Leu | Gln | Ala | Arg | Ser | Gly | Ser | Phe | Trp |
| | | 195 | | | | | 200 | | | | | 205 | | | |
| Gly | Ile | Thr | Gly | Pro | Pro | Gly | Ala | Pro | Gly | His | Val | Thr | Pro | Asp | Glu |
| | 210 | | | | | 215 | | | | | 220 | | | | |
| Trp | Glu | Met | Val | His | Lys | Ser | Val | Leu | Thr | Gln | Cys | Asp | Glu | Pro | Ile |
| 225 | | | | | 230 | | | | | 235 | | | | | 240 |
| Asp | Gly | Val | Asp | Asp | Gly | Val | Leu | Glu | Asp | Pro | Thr | Leu | Cys | Gln | Tyr |
| | | | | 245 | | | | | 250 | | | | | 255 | |
| Arg | Pro | Glu | Ala | Leu | Ile | Cys | Gly | Lys | Gly | Gln | Thr | Glu | Asn | Cys | Leu |
| | | | 260 | | | | | 265 | | | | | 270 | | |
| Thr | Lys | Ala | Lys | Ile | Glu | Thr | Val | Arg | Lys | Val | Phe | Ser | Pro | Leu | Tyr |
| | | 275 | | | | | 280 | | | | | 285 | | | |
| Thr | Thr | Asn | Glu | Thr | Tyr | Val | Tyr | Pro | Arg | Ala | Val | Pro | Gly | Ala | Asn |
| | 290 | | | | | 295 | | | | | 300 | | | | |
| Ala | Leu | Phe | Asn | Phe | Val | Val | Ala | Glu | Thr | Pro | Phe | Val | Tyr | Ser | Thr |
| 305 | | | | | 310 | | | | | 315 | | | | | 320 |
| Glu | Trp | Tyr | Gln | Tyr | Val | Ile | Trp | Glu | Asp | Pro | Glu | Trp | Asn | Pro | Asp |
| | | | | 325 | | | | | 330 | | | | | 335 | |
| Thr | Ile | Gly | Pro | Lys | Asp | Tyr | Asp | Arg | Gly | Ala | Glu | Met | Asn | Pro | Tyr |
| | | | 340 | | | | | 345 | | | | | 350 | | |
| Asp | Ile | Glu | Thr | Trp | Glu | Gly | Asp | Leu | Ser | Lys | Phe | Arg | Lys | Arg | Gly |
| | | 355 | | | | | 360 | | | | | 365 | | | |
| Asn | Lys | Met | Ile | His | Trp | His | Gly | Leu | Gln | Asp | Gly | Leu | Ile | Ser | Ala |
| | 370 | | | | | 375 | | | | | 380 | | | | |
| Glu | Asn | Ser | Asp | Asp | Tyr | Tyr | Asn | His | Val | Ser | Arg | Thr | Met | Gly | Leu |
| 385 | | | | | 390 | | | | | 395 | | | | | 400 |
| Asn | Ser | Ser | Gln | Leu | Asp | Gln | Phe | Tyr | Arg | Phe | Phe | Arg | Val | Ser | Gly |
| | | | | 405 | | | | | 410 | | | | | 415 | |

| | | | | | | | | | | | | | | |
|---|---|---|---|---|---|---|---|---|---|---|---|---|---|---|
| Cys | Gly | His | Cys | Ser | Ala | Gly | Asp | Gly | Ala | Ser | Arg | Ile | Gly | Asn | Asn |
| | | | 420 | | | | | 425 | | | | | 430 | | |
| Ala | Gly | Asn | Met | Gly | Gly | Lys | Thr | Ala | Asp | Thr | Asn | Val | Leu | Leu | Ala |
| | | 435 | | | | 440 | | | | | 445 | | | | |
| Ile | Val | Lys | Trp | Val | Glu | Glu | Gly | Val | Ala | Pro | Glu | Thr | Ile | Gly | Gly |
| | 450 | | | | 455 | | | | | 460 | | | | | |
| Tyr | Lys | Asn | Val | Gly | Gly | Thr | Ala | Asp | Gly | Ala | Phe | Asp | Tyr | Glu | Arg |
| 465 | | | | | 470 | | | | 475 | | | | | 480 | |
| Arg | His | Cys | Arg | Tyr | Pro | His | Arg | Asn | Val | Trp | Asp | Gly | Lys | Gly | Asn |
| | | | | 485 | | | | 490 | | | | | 495 | | |
| Val | Lys | Asp | Pro | Asp | Ser | Trp | Asn | Cys | Lys | Ile | | | | | |
| | | 500 | | | | | | 505 | | | | | | | |

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GTGAAATGGG TCGAGGAAGG                    20

( 2 ) INFORMATION FOR SEQ ID NO:21:

( i ) SEQUENCE CHARACTERISTICS:
        ( A ) LENGTH: 2284 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 241..1836

( x i ) SEQUENCE DESCRIPTION: SEQ ID NO:21:

| | |
|---|---|
| AGGTGTCATA CGCGTGTACC GAGGTATCAC CTCCTTTCTT GGACTATTGG TTGGTTGTTC | 60 |
| TATGAAGGAC CATCCGTTCA CCCCGCAGGA ACCAGGGACA TCTATGGCAA GAGTTTATCC | 120 |
| CGAGGCATGT ATATAATAAA GCTCTTGCCT CTCCTTCTCC TGACACTTCT CAGCCAGGCT | 180 |
| CAGGAGGCTG GCAGTGAGTT GAATATCTAT CTGTCTGATA GTTGTTCGTC ATCAGGCACT | 240 |

| | | | | | | | | | | | | | | | | |
|---|---|---|---|---|---|---|---|---|---|---|---|---|---|---|---|---|
| ATG | CGC | GTC | AAC | TTC | TCG | ACC | CTG | CTG | CTT | CCC | AGC | CTC | CTC | CAA | GGG | 288 |
| Met | Arg | Val | Asn | Phe | Ser | Thr | Leu | Leu | Leu | Pro | Ser | Leu | Leu | Gln | Gly | |
| | | 510 | | | | | 515 | | | | | 520 | | | | |
| CTA | GGT | GCA | TGC | GCA | GCT | CCC | AAC | AAA | GGC | AAC | GAT | GAT | TTT | GCC | GCG | 336 |
| Leu | Gly | Ala | Cys | Ala | Ala | Pro | Asn | Lys | Gly | Asn | Asp | Asp | Phe | Ala | Ala | |
| | | 525 | | | | 530 | | | | | 535 | | | | | |
| AAA | TGC | GCC | AGC | CTC | AAG | AAG | TCG | CTC | AAA | CTC | CCC | GGC | ACC | ACC | GTA | 384 |
| Lys | Cys | Ala | Ser | Leu | Lys | Lys | Ser | Leu | Lys | Leu | Pro | Gly | Thr | Thr | Val | |
| 540 | | | | | 545 | | | | | 550 | | | | | 555 | |
| TAC | TTC | ACC | CAG | CAT | GTC | TCG | GCT | GGT | ACC | AAC | ATC | ACT | TTC | CCC | GAT | 432 |
| Tyr | Phe | Thr | Gln | His | Val | Ser | Ala | Gly | Thr | Asn | Ile | Thr | Phe | Pro | Asp | |
| | | | | 560 | | | | | 565 | | | | | 570 | | |
| AAT | CAC | CCG | ACC | TGC | GGT | CCT | AAC | TAT | CAG | GTT | ACG | GAC | GTT | GAG | GTC | 480 |
| Asn | His | Pro | Thr | Cys | Gly | Pro | Asn | Tyr | Gln | Val | Thr | Asp | Val | Glu | Val | |
| | | | 575 | | | | | 580 | | | | | 585 | | | |
| TGC | CGC | GTG | GCC | ATG | TTA | GTC | AAG | ACG | GGA | CCC | GCC | TCA | AAC | GTT | AGC | 528 |

|     |     |     |     |     |     |     |     |     |     |     |     |     |     |     |     |
|-----|-----|-----|-----|-----|-----|-----|-----|-----|-----|-----|-----|-----|-----|-----|-----|
| Cys | Arg | Val | Ala | Met | Leu | Val | Lys | Thr | Gly | Pro | Ala | Ser | Asn | Val | Ser |
|     |     | 590 |     |     |     | 595 |     |     |     |     | 600 |     |     |     |     |

```
ATC GAA GCT TGG CTT CCC TTG AAC TGG ACA GGT CGG TTC TTA GGA ACT           576
Ile Glu Ala Trp Leu Pro Leu Asn Trp Thr Gly Arg Phe Leu Gly Thr
    605             610             615

GGC AAT GGT GGA TTA GCT GGC TGT ATG CCC TAC AAC GAT ATG GCG TAC           624
Gly Asn Gly Gly Leu Ala Gly Cys Met Pro Tyr Asn Asp Met Ala Tyr
620             625             630             635

GGC AAC AGT TTC GGC TTC GCC AGC GTT GGC ACG AAC AAC GGA CAT AAC           672
Gly Asn Ser Phe Gly Phe Ala Ser Val Gly Thr Asn Asn Gly His Asn
                640             645             650

GGA ACC TCA GGC CTA CCC ATG TAC CGC AAC CCA GGC GTG GTT GAG GAC           720
Gly Thr Ser Gly Leu Pro Met Tyr Arg Asn Pro Gly Val Val Glu Asp
            655             660             665

TTT GCC TAT CGT GCG GTG CAC GCT GGT GCT GTT ATC GGA AAG AAG ATC           768
Phe Ala Tyr Arg Ala Val His Ala Gly Ala Val Ile Gly Lys Lys Ile
        670             675             680

ACC CAG GGC TTT TAC GGC AAG AAG TTC AAG TCC TAC TTT CTC GGC TGC           816
Thr Gln Gly Phe Tyr Gly Lys Lys Phe Lys Ser Tyr Phe Leu Gly Cys
    685             690             695

TCG ACA GGA GGA CGT CAA GCA ATG AAG TTG GCA CAG AGC TTC CCC GAG           864
Ser Thr Gly Gly Arg Gln Ala Met Lys Leu Ala Gln Ser Phe Pro Glu
700             705             710             715

GAT TAC GAT GGC TAT GTG GCA GGT GCT CCG GCT ATG CGC TGG AAC GGT           912
Asp Tyr Asp Gly Tyr Val Ala Gly Ala Pro Ala Met Arg Trp Asn Gly
                720             725             730

CTT CAG GCA CGC TCT GGA AGT TTC TGG GGC ATC ACC GGC CCC CCT GGA           960
Leu Gln Ala Arg Ser Gly Ser Phe Trp Gly Ile Thr Gly Pro Pro Gly
            735             740             745

GCT CCT GGC CAT GTG ACT CCA GAC GAG TGG GAA ATG GTG CAC AAG AGC          1008
Ala Pro Gly His Val Thr Pro Asp Glu Trp Glu Met Val His Lys Ser
        750             755             760

GTC CTG ACT CAG TGC GAC GAG CCC ATT GAT GGC GTC GAT GAC GGC GTG          1056
Val Leu Thr Gln Cys Asp Glu Pro Ile Asp Gly Val Asp Asp Gly Val
    765             770             775

CTT GAG GAC CCC ACC CTC TGT CAG TAC CGC CCT GAG GCT CTC ATC TGC          1104
Leu Glu Asp Pro Thr Leu Cys Gln Tyr Arg Pro Glu Ala Leu Ile Cys
780             785             790             795

GGT AAG GGC CAG ACC GAG AAT TGC CTG ACC AAG GCC AAG ATT GAG ACG          1152
Gly Lys Gly Gln Thr Glu Asn Cys Leu Thr Lys Ala Lys Ile Glu Thr
                800             805             810

GTC CGC AAA GTC TTT TCT CCC CTA TAC ACC ACG AAT GAG ACA TAC GTC          1200
Val Arg Lys Val Phe Ser Pro Leu Tyr Thr Thr Asn Glu Thr Tyr Val
            815             820             825

TAC CCT CGA GCG GTT CCT GGT GCT AAC GCT CTC TTT AAC TTT GTT GTC          1248
Tyr Pro Arg Ala Val Pro Gly Ala Asn Ala Leu Phe Asn Phe Val Val
        830             835             840

GCC GAG ACA CCA TTC GTT TAC TCC ACA GAA TGG TAC CAG TAT GTC ATC          1296
Ala Glu Thr Pro Phe Val Tyr Ser Thr Glu Trp Tyr Gln Tyr Val Ile
    845             850             855

TGG GAA GAC CCT GAG TGG AAT CCT GAC ACT ATT GGG CCC AAG GAC TAT          1344
Trp Glu Asp Pro Glu Trp Asn Pro Asp Thr Ile Gly Pro Lys Asp Tyr
860             865             870             875

GAT AGA GGT GCC GAG ATG AAC CCC TAT GAC ATT GAG ACT TGG GAG GGA          1392
Asp Arg Gly Ala Glu Met Asn Pro Tyr Asp Ile Glu Thr Trp Glu Gly
                880             885             890

GAC CTG TCT AAG TTC CGC AAG CGT GGC AAC AAG ATG ATT CAC TGG CAC          1440
Asp Leu Ser Lys Phe Arg Lys Arg Gly Asn Lys Met Ile His Trp His
            895             900             905

GGC CTT CAG GAC GGA CTC ATC AGC GCC GAG AAC TCA GAC GAT TAT TAT          1488
```

| | | | | | | | | | | | | | | | | |
|---|---|---|---|---|---|---|---|---|---|---|---|---|---|---|---|---|
| Gly | Leu | Gln | Asp | Gly | Leu | Ile | Ser | Ala | Glu | Asn | Ser | Asp | Asp | Tyr | Tyr | |
| | | 910 | | | | 915 | | | | | 920 | | | | | |

| AAT | CAC | GTG | TCT | CGA | ACA | ATG | GGC | CTC | AAT | AGT | AGC | CAG | CTG | GAC | CAG | 1536 |
|---|---|---|---|---|---|---|---|---|---|---|---|---|---|---|---|---|
| Asn | His | Val | Ser | Arg | Thr | Met | Gly | Leu | Asn | Ser | Ser | Gln | Leu | Asp | Gln | |
| | 925 | | | | | 930 | | | | | 935 | | | | | |

| TTT | TAT | AGG | TTC | TTC | CGC | GTC | AGT | GGG | TGT | GGC | CAT | TGC | AGC | GCC | GGA | 1584 |
|---|---|---|---|---|---|---|---|---|---|---|---|---|---|---|---|---|
| Phe | Tyr | Arg | Phe | Phe | Arg | Val | Ser | Gly | Cys | Gly | His | Cys | Ser | Ala | Gly | |
| 940 | | | | | 945 | | | | | 950 | | | | | 955 | |

| GAC | GGG | GCT | TCT | CGC | ATT | GGA | AAC | AAC | GCC | GGA | AAC | ATG | GGC | GGC | AAG | 1632 |
|---|---|---|---|---|---|---|---|---|---|---|---|---|---|---|---|---|
| Asp | Gly | Ala | Ser | Arg | Ile | Gly | Asn | Asn | Ala | Gly | Asn | Met | Gly | Gly | Lys | |
| | | | | 960 | | | | | 965 | | | | | 970 | | |

| ACG | GCA | GAT | ACT | AAT | GTG | CTT | CTG | GCT | ATT | GTG | AAA | TGG | GTC | GAG | GAA | 1680 |
|---|---|---|---|---|---|---|---|---|---|---|---|---|---|---|---|---|
| Thr | Ala | Asp | Thr | Asn | Val | Leu | Leu | Ala | Ile | Val | Lys | Trp | Val | Glu | Glu | |
| | | | 975 | | | | | 980 | | | | | 985 | | | |

| GGC | GTT | GCG | CCA | GAA | ACG | ATT | GGG | GGC | TAC | AAG | AAC | GTC | GGC | GGA | ACT | 1728 |
|---|---|---|---|---|---|---|---|---|---|---|---|---|---|---|---|---|
| Gly | Val | Ala | Pro | Glu | Thr | Ile | Gly | Gly | Tyr | Lys | Asn | Val | Gly | Gly | Thr | |
| | | 990 | | | | | 995 | | | | | 1000 | | | | |

| GCA | GAT | GGC | GCT | TTT | GAC | TAT | GAG | CGT | AGG | CAT | TGC | CGA | TAC | CCA | CAC | 1776 |
|---|---|---|---|---|---|---|---|---|---|---|---|---|---|---|---|---|
| Ala | Asp | Gly | Ala | Phe | Asp | Tyr | Glu | Arg | Arg | His | Cys | Arg | Tyr | Pro | His | |
| | 1005 | | | | | 1010 | | | | | 1015 | | | | | |

| CGC | AAT | GTC | TGG | GAC | GGG | AAG | GGG | AAT | GTG | AAG | GAT | CCC | GAT | AGC | TGG | 1824 |
|---|---|---|---|---|---|---|---|---|---|---|---|---|---|---|---|---|
| Arg | Asn | Val | Trp | Asp | Gly | Lys | Gly | Asn | Val | Lys | Asp | Pro | Asp | Ser | Trp | |
| 1020 | | | | | 1025 | | | | | 1030 | | | | | 1035 | |

| AAC | TGT | AAG | ATC | TGAGGTGTGG | CCCTAGGCTT | TTGTGGCTGT | CGTTAGGTGG | 1876 |
|---|---|---|---|---|---|---|---|---|
| Asn | Cys | Lys | Ile | | | | | |

| CATACGTATA | TAAGAGGATC | ACTGTGAACA | TGCTTTATGT | TGTGCAAGAA | TTGATTGAGA | 1936 |
|---|---|---|---|---|---|---|
| ATCAGATTGA | GCTTGCAGAG | CCAAGGCAAA | TAGACCCAAC | TGTTGACGAG | ATCTTGGCCG | 1996 |
| AAGGTAGAGG | CAACGGGGAG | AGAGACCATG | GAAGACAAGG | CGTAGAAAAT | GGCCGGGGAA | 2056 |
| GACGGGCTGT | CGGCGATGGA | GTAGCAACAG | CTGTCACTGG | TGGTCAATGA | CTACACTTCT | 2116 |
| GAGCGGCGAG | AGATTATAGG | GACCGCACAC | AGGCCATCAT | TCCCGATAA | CTAATGGAGA | 2176 |
| CGCAATGGAG | CGATGTTTAA | ATGCGACAAG | ACTGCCATCA | TCTAGGTACT | TCATGCGTCG | 2236 |
| CTAAACGCAC | CAATGCTGCG | CTGCTCATGA | TTGTAAACTT | AGTTTATA | | 2284 |

(2) INFORMATION FOR SEQ ID NO:22:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:22:

| Met | Arg | Val | Asn | Phe | Ser | Thr | Leu | Leu | Leu | Pro | Ser | Leu | Leu | Gln | Gly |
|---|---|---|---|---|---|---|---|---|---|---|---|---|---|---|---|
| 1 | | | | 5 | | | | | 10 | | | | | 15 | |

| Leu | Gly | Ala | Cys | Ala | Ala | Pro | Asn | Lys | Gly | Asn | Asp | Asp | Phe | Ala | Ala |
|---|---|---|---|---|---|---|---|---|---|---|---|---|---|---|---|
| | | | 20 | | | | | 25 | | | | | 30 | | |

| Lys | Cys | Ala | Ser | Leu | Lys | Lys | Ser | Leu | Lys | Leu | Pro | Gly | Thr | Thr | Val |
|---|---|---|---|---|---|---|---|---|---|---|---|---|---|---|---|
| | | 35 | | | | | 40 | | | | | 45 | | | |

| Tyr | Phe | Thr | Gln | His | Val | Ser | Ala | Gly | Thr | Asn | Ile | Thr | Phe | Pro | Asp |
|---|---|---|---|---|---|---|---|---|---|---|---|---|---|---|---|
| | 50 | | | | | 55 | | | | | 60 | | | | |

| Asn | His | Pro | Thr | Cys | Gly | Pro | Asn | Tyr | Gln | Val | Thr | Asp | Val | Glu | Val |
|---|---|---|---|---|---|---|---|---|---|---|---|---|---|---|---|
| 65 | | | | 70 | | | | | 75 | | | | | 80 | |

| Cys | Arg | Val | Ala | Met | Leu | Val | Lys | Thr | Gly | Pro | Ala | Ser | Asn | Val | Ser |
|---|---|---|---|---|---|---|---|---|---|---|---|---|---|---|---|
| | | | 85 | | | | | 90 | | | | | 95 | | |

| Ile | Glu | Ala | Trp | Leu | Pro | Leu | Asn | Trp | Thr | Gly | Arg | Phe | Leu | Gly | Thr |
|---|---|---|---|---|---|---|---|---|---|---|---|---|---|---|---|
| | | | 100 | | | | | 105 | | | | | 110 | | |

```
Gly  Asn  Gly  Gly  Leu  Ala  Gly  Cys  Met  Pro  Tyr  Asn  Asp  Met  Ala  Tyr
          115                      120                      125

Gly  Asn  Ser  Phe  Gly  Phe  Ala  Ser  Val  Gly  Thr  Asn  Asn  Gly  His  Asn
     130                      135                      140

Gly  Thr  Ser  Gly  Leu  Pro  Met  Tyr  Arg  Asn  Pro  Gly  Val  Val  Glu  Asp
145                      150                      155                      160

Phe  Ala  Tyr  Arg  Ala  Val  His  Ala  Gly  Ala  Val  Ile  Gly  Lys  Lys  Ile
                    165                      170                      175

Thr  Gln  Gly  Phe  Tyr  Gly  Lys  Lys  Phe  Lys  Ser  Tyr  Phe  Leu  Gly  Cys
               180                      185                      190

Ser  Thr  Gly  Gly  Arg  Gln  Ala  Met  Lys  Leu  Ala  Gln  Ser  Phe  Pro  Glu
          195                      200                      205

Asp  Tyr  Asp  Gly  Tyr  Val  Ala  Gly  Ala  Pro  Ala  Met  Arg  Trp  Asn  Gly
     210                      215                      220

Leu  Gln  Ala  Arg  Ser  Gly  Ser  Phe  Trp  Gly  Ile  Thr  Gly  Pro  Pro  Gly
225                      230                      235                      240

Ala  Pro  Gly  His  Val  Thr  Pro  Asp  Glu  Trp  Glu  Met  Val  His  Lys  Ser
                    245                      250                      255

Val  Leu  Thr  Gln  Cys  Asp  Glu  Pro  Ile  Asp  Gly  Val  Asp  Asp  Gly  Val
               260                      265                      270

Leu  Glu  Asp  Pro  Thr  Leu  Cys  Gln  Tyr  Arg  Pro  Glu  Ala  Leu  Ile  Cys
          275                      280                      285

Gly  Lys  Gly  Gln  Thr  Glu  Asn  Cys  Leu  Thr  Lys  Ala  Lys  Ile  Glu  Thr
     290                      295                      300

Val  Arg  Lys  Val  Phe  Ser  Pro  Leu  Tyr  Thr  Thr  Asn  Glu  Thr  Tyr  Val
305                      310                      315                      320

Tyr  Pro  Arg  Ala  Val  Pro  Gly  Ala  Asn  Ala  Leu  Phe  Asn  Phe  Val  Val
                    325                      330                      335

Ala  Glu  Thr  Pro  Phe  Val  Tyr  Ser  Thr  Glu  Trp  Tyr  Gln  Tyr  Val  Ile
               340                      345                      350

Trp  Glu  Asp  Pro  Glu  Trp  Asn  Pro  Asp  Thr  Ile  Gly  Pro  Lys  Asp  Tyr
          355                      360                      365

Asp  Arg  Gly  Ala  Glu  Met  Asn  Pro  Tyr  Asp  Ile  Glu  Thr  Trp  Glu  Gly
     370                      375                      380

Asp  Leu  Ser  Lys  Phe  Arg  Lys  Arg  Gly  Asn  Lys  Met  Ile  His  Trp  His
385                      390                      395                      400

Gly  Leu  Gln  Asp  Gly  Leu  Ile  Ser  Ala  Glu  Asn  Ser  Asp  Tyr  Tyr
                    405                      410                      415

Asn  His  Val  Ser  Arg  Thr  Met  Gly  Leu  Asn  Ser  Ser  Gln  Leu  Asp  Gln
               420                      425                      430

Phe  Tyr  Arg  Phe  Phe  Arg  Val  Ser  Gly  Cys  Gly  His  Cys  Ser  Ala  Gly
          435                      440                      445

Asp  Gly  Ala  Ser  Arg  Ile  Gly  Asn  Asn  Ala  Gly  Asn  Met  Gly  Gly  Lys
     450                      455                      460

Thr  Ala  Asp  Thr  Asn  Val  Leu  Leu  Ala  Ile  Val  Lys  Trp  Val  Glu  Glu
465                      470                      475                      480

Gly  Val  Ala  Pro  Glu  Thr  Ile  Gly  Gly  Tyr  Lys  Asn  Val  Gly  Gly  Thr
                    485                      490                      495

Ala  Asp  Gly  Ala  Phe  Asp  Tyr  Glu  Arg  Arg  His  Cys  Arg  Tyr  Pro  His
               500                      505                      510

Arg  Asn  Val  Trp  Asp  Gly  Lys  Gly  Asn  Val  Lys  Asp  Pro  Asp  Ser  Trp
          515                      520                      525

Asn  Cys  Lys  Ile
```

5 3 0

( 2 ) INFORMATION FOR SEQ ID NO:23:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

| | | | | | |
|---|---|---|---|---|---|
| AGGTGTCATA | CGCGTGTACC | GAGGTATCAC | CTCCTTTCTT | GGACTATTGG | TTGGTTGTTC | 60 |
| TATGAAGGAC | CATCCGTTCA | CCCCGCAGGA | ACCAGGGACA | TCTATGGCAA | GAGTTTATCC | 120 |
| CGAGGCATGT | ATATAATAAA | GCTCTTGCCT | CTCCTTCTCC | TGACACTTCT | CAGCCAGGCT | 180 |
| CAGGAGGCTG | GCAGTGAGTT | GAATATCTAT | CTGTCTGATA | GTTGTTCGTC | ATCAGGCACT | 240 |

( 2 ) INFORMATION FOR SEQ ID NO:24:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

ATGCGCGTC      9

( 2 ) INFORMATION FOR SEQ ID NO:25:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

ATACGCGTC      9

( 2 ) INFORMATION FOR SEQ ID NO:26:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GGCACTATAC  GCGTC      15

( 2 ) INFORMATION FOR SEQ ID NO:27:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

AACAAAGGCA AC                                                                                                         12

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:28:

Asn Lys Gly Asn
    1

( 2 ) INFORMATION FOR SEQ ID NO:29:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

AACCCCGGGA AC                                                                                                         12

( 2 ) INFORMATION FOR SEQ ID NO:30:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

GCAGCTCCCA ACCCCGGGAA CGATGATT                                                                                        28